United States Patent
Leu et al.

(10) Patent No.: US 11,485,776 B2
(45) Date of Patent: Nov. 1, 2022

(54) ANTIBODIES AGAINST INFECTIOUS DISEASES

(71) Applicant: TAIPEI MEDICAL UNIVERSITY, Taipei (TW)

(72) Inventors: Sy-Jye Leu, Taipei (CN); Yi-Yuan Yang, Taipei (CN); Yu-Ching Lee, New Taipei (CN); Ching-Hua Su, Taipei (CN); Ko-Jiunn Liu, Taichung (CN); Hsiu-Jung Lo, New Taipei (CN); Yun-Liang Yang, New Taipei (CN)

(73) Assignee: TAIPEI MEDICAL UNIVERSITY, Taipei (TW)

( * ) Notice: Subject to any disclaimer, the term of this patent is extended or adjusted under 35 U.S.C. 154(b) by 0 days.

(21) Appl. No.: 16/937,447

(22) Filed: Jul. 23, 2020

(65) Prior Publication Data
US 2021/0079072 A1    Mar. 18, 2021

Related U.S. Application Data

(62) Division of application No. 15/563,614, filed as application No. PCT/CN2016/078238 on Apr. 1, 2016, now Pat. No. 10,766,951.

(60) Provisional application No. 62/141,412, filed on Apr. 1, 2015.

(51) Int. Cl.
| | | |
|---|---|---|
| *C07K 16/14* | (2006.01) |
| *C12N 9/88* | (2006.01) |
| *G01N 33/569* | (2006.01) |
| *A61K 39/00* | (2006.01) |
| *C12N 9/60* | (2006.01) |
| *C07K 16/18* | (2006.01) |
| *G01N 33/573* | (2006.01) |
| *A61K 39/395* | (2006.01) |
| *C07K 16/02* | (2006.01) |
| *A61P 31/10* | (2006.01) |
| *A61K 45/06* | (2006.01) |
| *C07K 16/40* | (2006.01) |

(52) U.S. Cl.
CPC .......... *C07K 16/14* (2013.01); *A61K 39/0002* (2013.01); *A61K 39/395* (2013.01); *A61K 45/06* (2013.01); *A61P 31/10* (2018.01); *C07K 16/02* (2013.01); *C07K 16/18* (2013.01); *C07K 16/40* (2013.01); *C12N 9/60* (2013.01); *C12N 9/88* (2013.01); *C12Y 402/01011* (2013.01); *G01N 33/56938* (2013.01); *G01N 33/56944* (2013.01); *G01N 33/56961* (2013.01); *G01N 33/573* (2013.01); *A61K 2039/505* (2013.01); *C07K 2317/23* (2013.01); *C07K 2317/24* (2013.01); *C07K 2317/33* (2013.01); *C07K 2317/34* (2013.01); *C07K 2317/565* (2013.01); *C07K 2317/622* (2013.01); *C07K 2317/76* (2013.01); *C07K 2317/92* (2013.01); *G01N 2333/40* (2013.01); *G01N 2333/988* (2013.01)

(58) Field of Classification Search
None
See application file for complete search history.

(56) References Cited

FOREIGN PATENT DOCUMENTS

| EP | 2 680 002 A1 | 1/2014 | |
| WO | WO-2008109833 A2 * | 9/2008 | ............. C07K 14/40 |

OTHER PUBLICATIONS

Pitarch, aida et al., Journal of Proteome research (2014), vol. 13, p. 5165-5184.
European Search Report dated Jul. 5, 2018 issued to the EP counterpart (Appln. No. 16771407.0).
Office action dated Mar. 24, 2020 issued to the JP counterpart (Appln. No. 2018-502307).
English machine translation of the Office action dated Mar. 24, 2020 issued to the JP counterpart (Appln. No. 2018-502307).

* cited by examiner

*Primary Examiner* — Brian Gangle
(74) *Attorney, Agent, or Firm* — WPAT, P.C.; Anthony King

(57) ABSTRACT

The invention provides anti-CaENO1 antibodies and humanized antibodies as effective diagnostic agent or therapeutic treatment against infections caused by *Candida* spp. (preferably *Candida. albicans, Candida tropicalis*), fluconazole resistance *Candida* spp., *Streptococcus*, or *Staphylococcus*.

6 Claims, 18 Drawing Sheets
Specification includes a Sequence Listing.

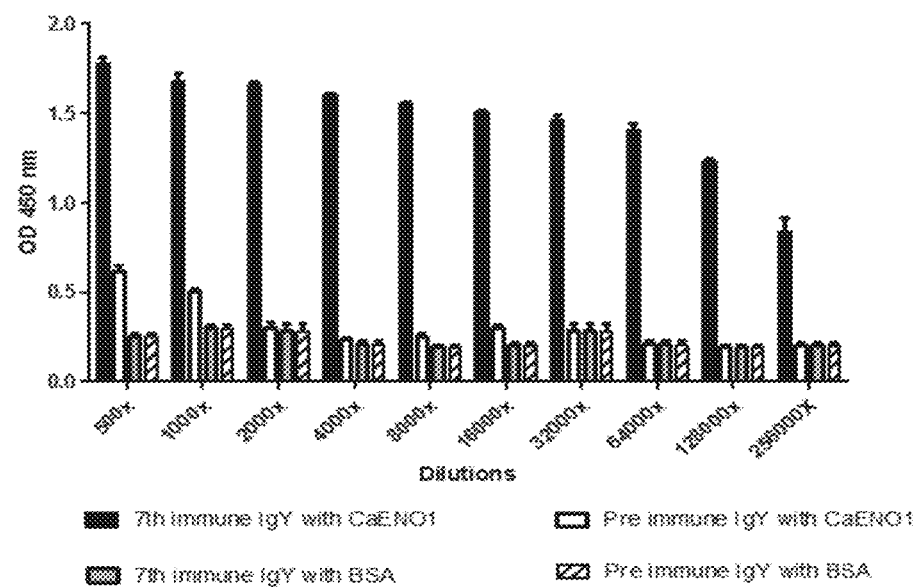
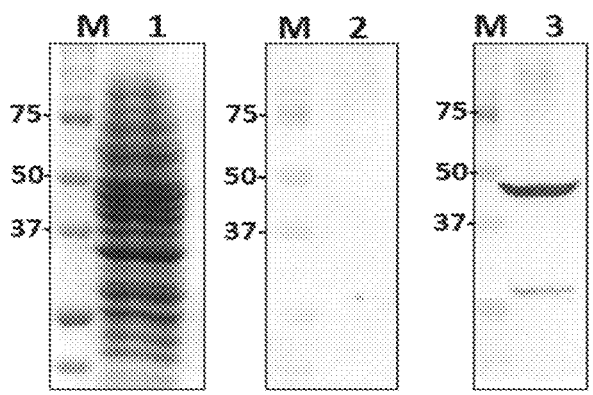
Fig. 2

```
                        <-FR1------>  <-CDR1->  <---FR2--->  <-CDR2->  <----------FR3----------->  <--CDR3-->  <--FR4-->
VL      ALTQPSSVSANPGGTVKITC  SGDSSYYG  WYQQKAPGSAPVTVIY  DNTNRPS  NIPSRFSGSKSGSTATLTITGVRADDNAVYYC  ASTDSSSTAGI  PGAGTTLTVL  (SEQ ID NO: 21)
CaS1 L  -----------------I-  -G-GS---  -------S--------  -S-NQ--  -----------Q------F--------------  G-R---YVGV  ----------  (SEQ ID NO: 23)

<--FR1-->  <-CDR1->  <----FR2---->  <--CDR2-->  <---------FR3---------->  <---CDR3--->  <--FR4-->
VH      AVTLDESGGGLQTPGGALSLVCKASGFTFS  SYHML  WVRQAPGKGLEWVA  GIDATGGYTRYAAAVKG  RATISRDNGQSTVRLQLNNLRAEDTATYYCAR  ETAGAIDA GGHGTEVIVSS  (SEQ ID NO: 22)
CaS1 H  ------------------I-  --H-S-I  D-G-Q  -----  -GSS--S--S-------  ------------------------------  SAGGTVYGQCSD  --------  (SEQ ID NO: 24)
```

Fig. 3

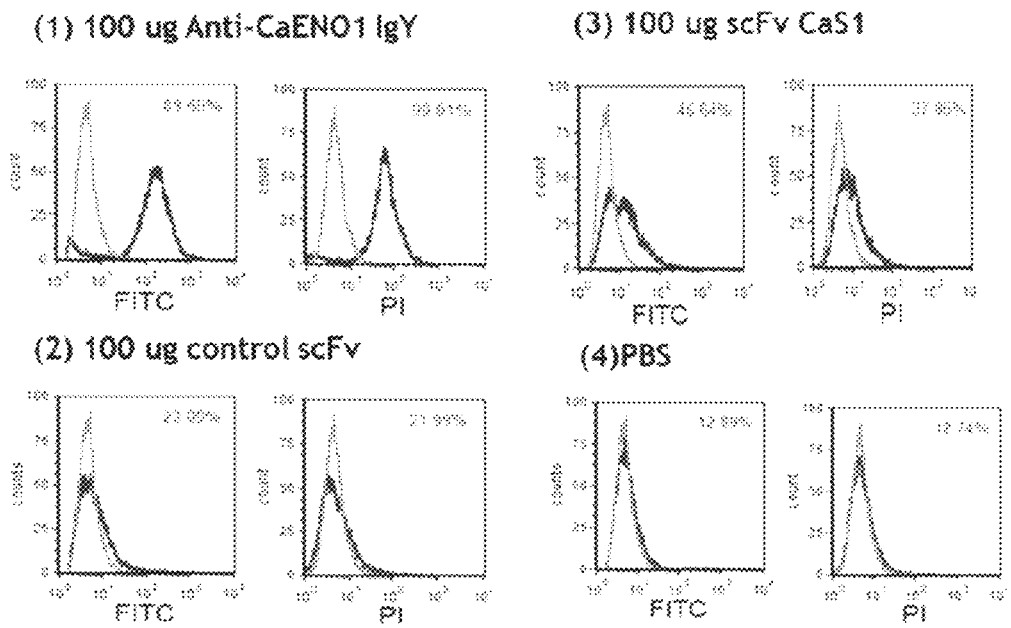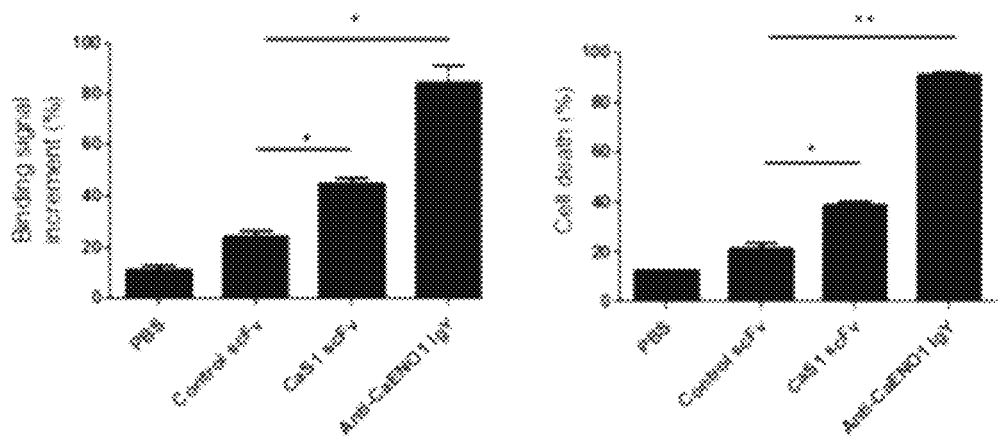
Fig. 7

(A)
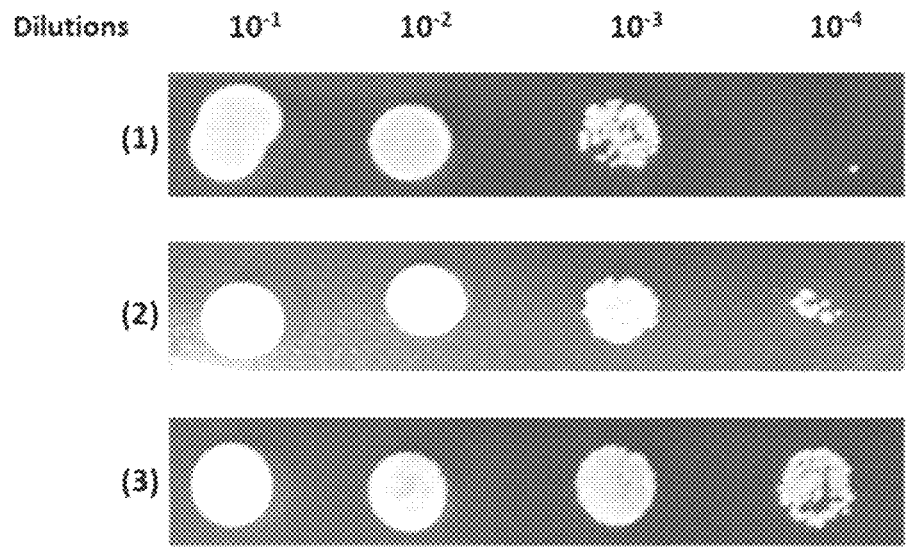
(B)
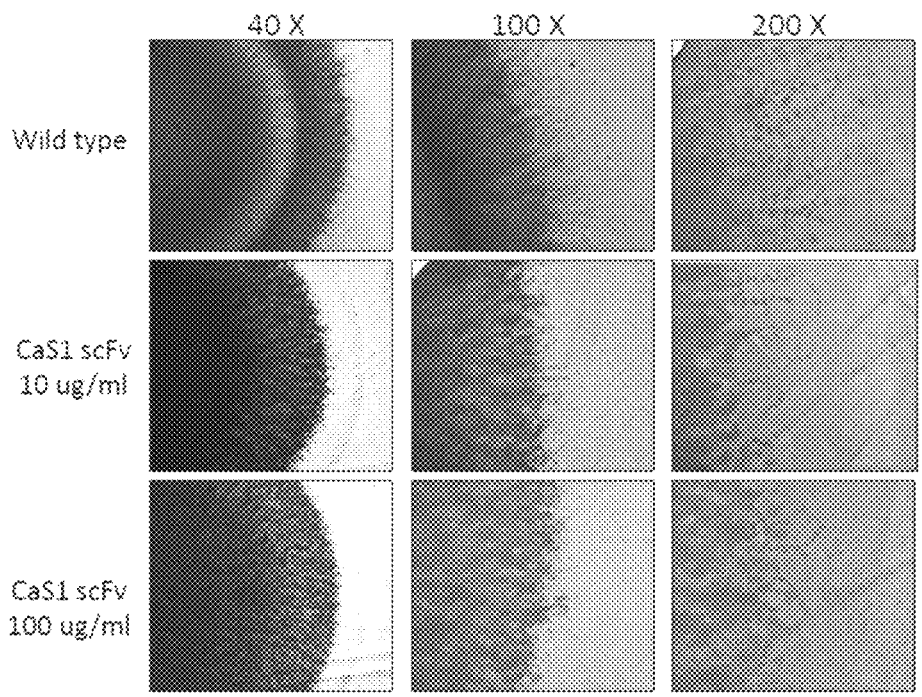
Fig. 9

CaENO1 amino acids

MSYATKIHARYVYDSRGNPTVEVDFTTDKGLFRSIVPSGASTGVHEALELRDGDKSKWLGKGVLKAVAN
VNDIIAPALIKAKIDVVDQAKIDEFLLSLDGTPNKSKLGANAILGVSLAAANAAAAAQGIPLYKHIANISNAK
KGKFVLPVPFQNVLNGGSHAGGALAFQEFMIAPTGVSTFSEALRIGSEVYHNLKSLTKKKYGQSAGNV
GDEGGVAPDIKTPKEALDLIMDAIDKAGYKGKVGIAMDVASSEFYKDGKYDLDFKNPESDPSKWLSGPQ
LADLYEQLISEYPIVSIEDPFAEDDWDAWVHFFERVGDKIQIVGDDLTVTNPTRIKTAIEKKAANALLLKVN
QIGTLTESIQAANDSYAAGWGVMVSHRSGETEDTFIADLSVGLRSGQIKTGAPARSERLAKLNQILRIEE
ELGSEAIYAGKDFQKASQL (SEQ ID NO: 25)

KGKVGIAMDV (SEQ ID NO: 26)
PQLADLYEQLISEYP (SEQ ID NO: 27)
AEDDWDAWVHFFERVGDKIQIVGDDLTVTNPTRIKTAIEKKAANALLLKVNQIGTLTESIQAANDSYAAG
WGVMVSHRSGETEDTFIADLSVGLRSGQIKTGAPARSERLAKLNQILRIEEELGSEAIYAGKDFQKASQL
(SEQ ID NO: 28)

Fig. 16

SEQUENCE LISTING

```
<160> NUMBER OF SEQ ID NOS: 29

<210> SEQ ID NO 1
<211> LENGTH: 10
<212> TYPE: PRT
<213> ORGANISM: Candida albicans spp.

<400> SEQUENCE: 1

Leu Tyr Glu Gln Leu Ile Ser Glu Tyr Pro
1               5                   10

<210> SEQ ID NO 2
<211> LENGTH: 10
<212> TYPE: PRT
<213> ORGANISM: Candida albicans spp.

<400> SEQUENCE: 2

Pro Gln Leu Ala Asp Leu Tyr Glu Gln Leu
1               5                   10
```

-continued

```
<210> SEQ ID NO 3
<211> LENGTH: 10
<212> TYPE: PRT
<213> ORGANISM: Candida albicans spp.

<400> SEQUENCE: 3

Lys Gly Lys Val Gly Ile Ala Met Asp Val
1               5                   10

<210> SEQ ID NO 4
<211> LENGTH: 15
<212> TYPE: PRT
<213> ORGANISM: Candida albicans spp.

<400> SEQUENCE: 4

Pro Gln Leu Ala Asp Leu Tyr Glu Gln Leu Ile Ser Glu Tyr Pro
1               5                   10                  15

<210> SEQ ID NO 5
<211> LENGTH: 5
<212> TYPE: PRT
<213> ORGANISM: Artificial Sequence
<220> FEATURE:
<223> OTHER INFORMATION: L-CDR1

<400> SEQUENCE: 5

Ser Gly Ser Tyr Gly
1               5

<210> SEQ ID NO 6
<211> LENGTH: 3
<212> TYPE: PRT
<213> ORGANISM: Artificial Sequence
<220> FEATURE:
<223> OTHER INFORMATION: L-CDR2

<400> SEQUENCE: 6

Ser Asn Asn
1

<210> SEQ ID NO 7
<211> LENGTH: 10
<212> TYPE: PRT
<213> ORGANISM: Artificial Sequence
<220> FEATURE:
<223> OTHER INFORMATION: L-CDR3

<400> SEQUENCE: 7

Gly Ser Arg Asp Ser Ser Tyr Val Gly Val
1               5                   10

<210> SEQ ID NO 8
<211> LENGTH: 8
<212> TYPE: PRT
<213> ORGANISM: Artificial Sequence
<220> FEATURE:
<223> OTHER INFORMATION: H-CDR1

<400> SEQUENCE: 8

Gly Phe Thr Phe Ile Asp Tyr Gly
1               5

<210> SEQ ID NO 9
<211> LENGTH: 8
<212> TYPE: PRT
<213> ORGANISM: Artificial Sequence
<220> FEATURE:
```

<223> OTHER INFORMATION: H-CDR2

<400> SEQUENCE: 9

Ile Gly Ser Ser Gly Ser Ser Thr
1               5

<210> SEQ ID NO 10
<211> LENGTH: 21
<212> TYPE: PRT
<213> ORGANISM: Artificial Sequence
<220> FEATURE:
<223> OTHER INFORMATION: H-CDR3

<400> SEQUENCE: 10

Ala Lys Ser Ala Gly Gly Tyr Cys Val Asn Gly Ala Gly Cys Asn Gly
1               5                   10                  15

Gly Ser Ile Asp Ala
            20

<210> SEQ ID NO 11
<211> LENGTH: 103
<212> TYPE: PRT
<213> ORGANISM: Artificial Sequence
<220> FEATURE:
<223> OTHER INFORMATION: amino acid sequence comprised in a light chain
      of an anti-CaENO1 scFv monoclonal antibody (CaS1)

<400> SEQUENCE: 11

Ala Leu Thr Gln Pro Ser Ser Val Ser Ala Asn Leu Gly Gly Thr Val
1               5                   10                  15

Lys Ile Thr Cys Ser Gly Gly Ser Gly Ser Tyr Gly Trp Tyr Gln Gln
            20                  25                  30

Lys Ser Pro Gly Ser Ala Pro Val Thr Val Ile Tyr Ser Asn Asn Gln
        35                  40                  45

Arg Pro Ser Asn Ile Pro Ser Arg Phe Ser Gly Ser Pro Ser Gly Ser
    50                  55                  60

Thr Gly Thr Leu Thr Ile Thr Gly Val Gln Ala Asp Asp Glu Ala Val
65                  70                  75                  80

Tyr Phe Cys Gly Ser Arg Asp Ser Ser Tyr Val Gly Val Phe Gly Ala
                85                  90                  95

Gly Thr Thr Leu Thr Val Leu
            100

<210> SEQ ID NO 12
<211> LENGTH: 128
<212> TYPE: PRT
<213> ORGANISM: Artificial Sequence
<220> FEATURE:
<223> OTHER INFORMATION: amino acid sequence comprised in a heavy chain
      of an anti-CaENO1 scFv monoclonal antibody (CaS1)

<400> SEQUENCE: 12

Thr Val Thr Leu Asp Glu Ser Gly Gly Gly Leu Gln Thr Pro Arg Gly
1               5                   10                  15

Ala Leu Ser Leu Val Cys Lys Ala Ser Gly Phe Thr Phe Ile Asp Tyr
            20                  25                  30

Gly Met Gln Trp Val Arg Gln Ala Pro Gly Lys Gly Leu Glu Trp Val
        35                  40                  45

Ala Gly Ile Gly Ser Ser Gly Ser Ser Thr Asn Tyr Gly Ala Ala Val
    50                  55                  60

Lys Gly Arg Ala Thr Ile Ser Arg Asp Asp Gly Gln Ser Thr Val Arg

```
                65                  70                  75                  80
Leu Gln Leu Asn Asn Leu Arg Ala Glu Asp Thr Gly Thr Tyr Tyr Cys
                    85                  90                  95

Ala Lys Ser Ala Gly Gly Tyr Cys Val Asn Gly Ala Gly Cys Asn Gly
                100                 105                 110

Gly Ser Ile Asp Ala Trp Gly His Gly Thr Glu Val Ile Val Ser Ser
                115                 120                 125

<210> SEQ ID NO 13
<211> LENGTH: 107
<212> TYPE: PRT
<213> ORGANISM: Artificial Sequence
<220> FEATURE:
<223> OTHER INFORMATION: hzCaS1-V1 scFv

<400> SEQUENCE: 13

Asp Ile Gln Leu Thr Gln Ser Pro Ser Ser Leu Ser Ala Ser Val Gly
1               5                   10                  15

Asp Arg Val Thr Ile Thr Cys Arg Ala Ser Ser Gly Ser Tyr Gly Leu
                20                  25                  30

Gly Trp Tyr Gln Gln Lys Pro Gly Lys Ala Pro Lys Arg Leu Ile Tyr
            35                  40                  45

Ser Asn Asn Ser Leu Gln Ser Gly Val Pro Ser Arg Phe Ser Gly Ser
        50                  55                  60

Gly Ser Gly Thr Glu Phe Thr Leu Thr Ile Ser Ser Leu Gln Pro Glu
65                  70                  75                  80

Asp Phe Ala Thr Tyr Tyr Cys Gly Ser Arg Asp Ser Ser Tyr Val Gly
                85                  90                  95

Val Phe Gly Gln Gly Thr Lys Val Glu Ile Lys
                100                 105

<210> SEQ ID NO 14
<211> LENGTH: 107
<212> TYPE: PRT
<213> ORGANISM: Artificial Sequence
<220> FEATURE:
<223> OTHER INFORMATION: hzCaS1-V3 scFv

<400> SEQUENCE: 14

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Gly Ser Tyr Gly Val
                20                  25                  30

Ala Trp Tyr Gln Gln Lys Pro Gly Lys Ala Pro Lys Leu Leu Ile Tyr
            35                  40                  45

Ser Asn Asn Phe Leu Tyr Ser Gly Val Pro Ser Arg Phe Ser Gly Ser
        50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gly Ser Arg Asp Ser Ser Tyr Val Gly
                85                  90                  95

Val Phe Gly Gln Gly Thr Lys Val Glu Ile Lys
                100                 105

<210> SEQ ID NO 15
<211> LENGTH: 128
<212> TYPE: PRT
<213> ORGANISM: Artificial Sequence
<220> FEATURE:
```

<223> OTHER INFORMATION: hzCaS1-V1 scFv

<400> SEQUENCE: 15

Glu Val Lys Leu Glu Glu Ser Gly Gly Gly Leu Val Gln Pro Gly Gly
1               5                   10                  15

Ser Met Lys Leu Ser Cys Ala Ala Ser Gly Phe Thr Phe Ile Asp Tyr
            20                  25                  30

Gly Met Asp Trp Val Arg Gln Ser Pro Glu Lys Gly Leu Glu Trp Val
        35                  40                  45

Ala Glu Ile Gly Ser Ser Gly Ser Ser Thr His Tyr Ala Glu Ser Val
    50                  55                  60

Lys Gly Arg Phe Thr Val Ser Arg Asp Asp Ser Lys Ser Ser Val Tyr
65                  70                  75                  80

Leu Gln Met Asn Ser Leu Arg Ala Glu Asp Thr Gly Ile Tyr Tyr Cys
                85                  90                  95

Ala Lys Ser Ala Gly Gly Tyr Cys Val Asn Gly Ala Gly Cys Asn Gly
            100                 105                 110

Gly Ser Ile Asp Ala Trp Gly Gln Gly Thr Leu Val Thr Val Ser Ala
        115                 120                 125

<210> SEQ ID NO 16
<211> LENGTH: 128
<212> TYPE: PRT
<213> ORGANISM: Artificial Sequence
<220> FEATURE:
<223> OTHER INFORMATION: hzCaS1-V3 scFv

<400> SEQUENCE: 16

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ile Asp Tyr
            20                  25                  30

Gly Ile His Trp Val Arg Gln Ala Pro Gly Lys Gly Leu Glu Trp Val
        35                  40                  45

Ala Gly Ile Gly Ser Ser Gly Ser Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Lys Ser Ala Gly Gly Tyr Cys Val Asn Gly Ala Gly Cys Asn Gly
            100                 105                 110

Gly Ser Ile Asp Ala Trp Gly Gln Gly Thr Leu Val Thr Val Ser Ser
        115                 120                 125

<210> SEQ ID NO 17
<211> LENGTH: 7
<212> TYPE: PRT
<213> ORGANISM: Artificial Sequence
<220> FEATURE:
<223> OTHER INFORMATION: Linker of anti-CaENO1-S Library

<400> SEQUENCE: 17

Gly Gln Ser Ser Arg Ser Ser
1               5

<210> SEQ ID NO 18
<211> LENGTH: 18
<212> TYPE: PRT

```
<213> ORGANISM: Artificial Sequence
<220> FEATURE:
<223> OTHER INFORMATION: Linker of anti-CaENO1-L Library

<400> SEQUENCE: 18

Gly Gln Ser Ser Arg Ser Ser Gly Gly Gly Ser Ser Gly Gly
1               5                   10                  15

Gly Ser

<210> SEQ ID NO 19
<211> LENGTH: 66
<212> TYPE: PRT
<213> ORGANISM: Artificial Sequence
<220> FEATURE:
<223> OTHER INFORMATION: epitope region of CaENO1

<400> SEQUENCE: 19

Asp Lys Ala Gly Tyr Lys Gly Lys Val Gly Ile Ala Met Asp Val Ala
1               5                   10                  15

Ser Ser Glu Phe Tyr Lys Asp Gly Lys Tyr Asp Leu Asp Phe Lys Asn
            20                  25                  30

Pro Glu Ser Asp Pro Ser Lys Trp Leu Ser Gly Pro Gln Leu Ala Asp
        35                  40                  45

Leu Tyr Glu Gln Leu Ile Ser Glu Tyr Pro Ile Val Ser Ile Glu Asp
    50                  55                  60

Pro Phe
65

<210> SEQ ID NO 20
<211> LENGTH: 137
<212> TYPE: PRT
<213> ORGANISM: Artificial Sequence
<220> FEATURE:
<223> OTHER INFORMATION: a fragment of plasminogen spanning amino acid
      residues 301 to 437

<400> SEQUENCE: 20

Ala Glu Asp Asp Trp Asp Ala Trp Val His Phe Phe Glu Arg Val Gly
1               5                   10                  15

Asp Lys Ile Gln Ile Val Gly Asp Asp Leu Thr Val Thr Asn Pro Thr
            20                  25                  30

Arg Ile Lys Thr Ala Ile Glu Lys Lys Ala Ala Asn Ala Leu Leu Leu
        35                  40                  45

Lys Val Asn Gln Ile Gly Thr Leu Thr Glu Ser Ile Gln Ala Ala Asn
    50                  55                  60

Asp Ser Tyr Ala Ala Gly Trp Gly Val Met Val Ser His Arg Ser Gly
65                  70                  75                  80

Glu Thr Glu Asp Thr Phe Ile Ala Asp Leu Ser Val Gly Leu Arg Ser
                85                  90                  95

Gly Gln Ile Lys Thr Gly Ala Pro Ala Arg Ser Glu Arg Leu Ala Lys
            100                 105                 110

Leu Asn Gln Ile Leu Arg Ile Glu Glu Glu Leu Gly Ser Glu Ala Ile
        115                 120                 125

Tyr Ala Gly Lys Asp Phe Gln Lys Ala
    130                 135

<210> SEQ ID NO 21
<211> LENGTH: 104
<212> TYPE: PRT
<213> ORGANISM: Gallus domesticus
```

<400> SEQUENCE: 21

```
Ala Leu Thr Gln Pro Ser Ser Val Ser Ala Asn Pro Gly Gly Thr Val
1               5                   10                  15

Lys Ile Thr Cys Ser Gly Asp Ser Ser Tyr Tyr Gly Trp Tyr Gln Gln
            20                  25                  30

Lys Ala Pro Gly Ser Ala Pro Val Thr Val Ile Tyr Asp Asn Thr Asn
        35                  40                  45

Arg Pro Ser Asn Ile Pro Ser Arg Phe Ser Gly Ser Lys Ser Gly Ser
    50                  55                  60

Thr Ala Thr Leu Thr Ile Thr Gly Val Arg Ala Asp Asp Asn Ala Val
65                  70                  75                  80

Tyr Tyr Cys Ala Ser Thr Asp Ser Ser Thr Ala Gly Ile Phe Gly
                85                  90                  95

Ala Gly Thr Thr Leu Thr Val Leu
            100
```

<210> SEQ ID NO 22
<211> LENGTH: 117
<212> TYPE: PRT
<213> ORGANISM: Gallus domesticus

<400> SEQUENCE: 22

```
Ala Val Thr Leu Asp Glu Ser Gly Gly Gly Leu Gln Thr Pro Gly Gly
1               5                   10                  15

Ala Leu Arg Leu Val Cys Lys Ala Ser Gly Phe Thr Phe Ser Ser Tyr
            20                  25                  30

Asp Met Leu Trp Val Arg Gln Ala Pro Gly Lys Gly Leu Glu Phe Val
        35                  40                  45

Ala Gly Ile Asp Asn Thr Gly Ser Tyr Thr His Tyr Gly Ala Ala Val
    50                  55                  60

Lys Gly Arg Ala Thr Ile Ser Arg Asp Asn Gly Gln Ser Thr Gly Arg
65                  70                  75                  80

Leu Gln Leu Asn Asn Leu Arg Ala Glu Asp Thr Ala Thr Tyr Tyr Cys
                85                  90                  95

Ala Lys Arg Thr Ala Gly Ser Ile Asp Ala Trp Gly His Gly Thr Glu
            100                 105                 110

Val Ile Val Ser Ser
        115
```

<210> SEQ ID NO 23
<211> LENGTH: 103
<212> TYPE: PRT
<213> ORGANISM: Gallus domesticus

<400> SEQUENCE: 23

```
Ala Leu Thr Gln Pro Ser Ser Val Ser Ala Asn Leu Gly Gly Thr Val
1               5                   10                  15

Lys Ile Thr Cys Ser Gly Gly Ser Gly Ser Tyr Gly Trp Tyr Gln Gln
            20                  25                  30

Lys Ser Pro Gly Ser Ala Pro Val Thr Val Ile Tyr Ser Asn Asn Gln
        35                  40                  45

Arg Pro Ser Asn Ile Pro Ser Arg Phe Ser Gly Ser Pro Ser Gly Ser
    50                  55                  60

Thr Gly Thr Leu Thr Ile Thr Gly Val Gln Ala Asp Asp Glu Ala Val
65                  70                  75                  80
```

```
Tyr Phe Cys Gly Ser Arg Asp Ser Ser Tyr Val Gly Val Phe Gly Ala
                85                  90                  95

Gly Thr Thr Leu Thr Val Leu
            100

<210> SEQ ID NO 24
<211> LENGTH: 128
<212> TYPE: PRT
<213> ORGANISM: Gallus domesticus

<400> SEQUENCE: 24

Thr Val Thr Leu Asp Glu Ser Gly Gly Leu Gln Thr Pro Arg Gly
1               5                   10                  15

Ala Leu Ser Leu Val Cys Lys Ala Ser Gly Phe Thr Phe Ile Asp Tyr
                20                  25                  30

Gly Met Gln Trp Val Arg Gln Ala Pro Gly Lys Gly Leu Glu Trp Val
            35                  40                  45

Ala Gly Ile Gly Ser Ser Gly Ser Ser Thr Asn Tyr Gly Ala Ala Val
        50                  55                  60

Lys Gly Arg Ala Thr Ile Ser Arg Asp Asp Gly Gln Ser Thr Val Arg
65                  70                  75                  80

Leu Gln Leu Asn Asn Leu Arg Ala Glu Asp Thr Gly Thr Tyr Tyr Cys
                85                  90                  95

Ala Lys Ser Ala Gly Gly Tyr Cys Val Asn Gly Ala Gly Cys Asn Gly
                100                 105                 110

Gly Ser Ile Asp Ala Trp Gly His Gly Thr Glu Val Ile Val Ser Ser
            115                 120                 125

<210> SEQ ID NO 25
<211> LENGTH: 440
<212> TYPE: PRT
<213> ORGANISM: Candida albicans spp.

<400> SEQUENCE: 25

Met Ser Tyr Ala Thr Lys Ile His Ala Arg Tyr Val Tyr Asp Ser Arg
1               5                   10                  15

Gly Asn Pro Thr Val Glu Val Asp Phe Thr Thr Asp Lys Gly Leu Phe
                20                  25                  30

Arg Ser Ile Val Pro Ser Gly Ala Ser Thr Gly Val His Glu Ala Leu
            35                  40                  45

Glu Leu Arg Asp Gly Asp Lys Ser Lys Trp Leu Gly Lys Gly Val Leu
        50                  55                  60

Lys Ala Val Ala Asn Val Asn Asp Ile Ile Ala Pro Ala Leu Ile Lys
65                  70                  75                  80

Ala Lys Ile Asp Val Val Asp Gln Ala Lys Ile Asp Glu Phe Leu Leu
                85                  90                  95

Ser Leu Asp Gly Thr Pro Asn Lys Ser Lys Leu Gly Ala Asn Ala Ile
                100                 105                 110

Leu Gly Val Ser Leu Ala Ala Ala Asn Ala Ala Ala Ala Ala Gln Gly
            115                 120                 125

Ile Pro Leu Tyr Lys His Ile Ala Asn Ile Ser Asn Ala Lys Lys Gly
        130                 135                 140

Lys Phe Val Leu Pro Val Pro Phe Gln Asn Val Leu Asn Gly Gly Ser
145                 150                 155                 160

His Ala Gly Gly Ala Leu Ala Phe Gln Glu Phe Met Ile Ala Pro Thr
                165                 170                 175
```

Gly Val Ser Thr Phe Ser Glu Ala Leu Arg Ile Gly Ser Glu Val Tyr
            180                 185                 190

His Asn Leu Lys Ser Leu Thr Lys Lys Tyr Gly Gln Ser Ala Gly
        195                 200                 205

Asn Val Gly Asp Glu Gly Val Ala Pro Asp Ile Lys Thr Pro Lys
210                 215                 220

Glu Ala Leu Asp Leu Ile Met Asp Ala Ile Asp Lys Ala Gly Tyr Lys
225                 230                 235                 240

Gly Lys Val Gly Ile Ala Met Asp Val Ala Ser Ser Glu Phe Tyr Lys
                245                 250                 255

Asp Gly Lys Tyr Asp Leu Asp Phe Lys Asn Pro Glu Ser Asp Pro Ser
            260                 265                 270

Lys Trp Leu Ser Gly Pro Gln Leu Ala Asp Leu Tyr Glu Gln Leu Ile
        275                 280                 285

Ser Glu Tyr Pro Ile Val Ser Ile Glu Asp Pro Phe Ala Glu Asp Asp
    290                 295                 300

Trp Asp Ala Trp Val His Phe Phe Glu Arg Val Gly Asp Lys Ile Gln
305                 310                 315                 320

Ile Val Gly Asp Asp Leu Thr Val Thr Asn Pro Thr Arg Ile Lys Thr
                325                 330                 335

Ala Ile Glu Lys Lys Ala Ala Asn Ala Leu Leu Leu Lys Val Asn Gln
            340                 345                 350

Ile Gly Thr Leu Thr Glu Ser Ile Gln Ala Ala Asn Asp Ser Tyr Ala
        355                 360                 365

Ala Gly Trp Gly Val Met Val Ser His Arg Ser Gly Glu Thr Glu Asp
    370                 375                 380

Thr Phe Ile Ala Asp Leu Ser Val Gly Leu Arg Ser Gly Gln Ile Lys
385                 390                 395                 400

Thr Gly Ala Pro Ala Arg Ser Glu Arg Leu Ala Lys Leu Asn Gln Ile
                405                 410                 415

Leu Arg Ile Glu Glu Leu Gly Ser Glu Ala Ile Tyr Ala Gly Lys
            420                 425                 430

Asp Phe Gln Lys Ala Ser Gln Leu
        435                 440

<210> SEQ ID NO 26
<211> LENGTH: 10
<212> TYPE: PRT
<213> ORGANISM: Candida albicans spp.

<400> SEQUENCE: 26

Lys Gly Lys Val Gly Ile Ala Met Asp Val
1               5                   10

<210> SEQ ID NO 27
<211> LENGTH: 15
<212> TYPE: PRT
<213> ORGANISM: Candida albicans spp.

<400> SEQUENCE: 27

Pro Gln Leu Ala Asp Leu Tyr Glu Gln Leu Ile Ser Glu Tyr Pro
1               5                   10                  15

<210> SEQ ID NO 28
<211> LENGTH: 140
<212> TYPE: PRT
<213> ORGANISM: Candida albicans spp.

```
<400> SEQUENCE: 28

Ala Glu Asp Asp Trp Asp Ala Trp Val His Phe Phe Glu Arg Val Gly
1               5                   10                  15

Asp Lys Ile Gln Ile Val Gly Asp Asp Leu Thr Val Thr Asn Pro Thr
            20                  25                  30

Arg Ile Lys Thr Ala Ile Glu Lys Lys Ala Ala Asn Ala Leu Leu Leu
        35                  40                  45

Lys Val Asn Gln Ile Gly Thr Leu Thr Glu Ser Ile Gln Ala Ala Asn
    50                  55                  60

Asp Ser Tyr Ala Ala Gly Trp Gly Val Met Val Ser His Arg Ser Gly
65              70                  75                  80

Glu Thr Glu Asp Thr Phe Ile Ala Asp Leu Ser Val Gly Leu Arg Ser
            85                  90                  95

Gly Gln Ile Lys Thr Gly Ala Pro Ala Arg Ser Glu Arg Leu Ala Lys
            100                 105                 110

Leu Asn Gln Ile Leu Arg Ile Glu Glu Glu Leu Gly Ser Glu Ala Ile
            115                 120                 125

Tyr Ala Gly Lys Asp Phe Gln Lys Ala Ser Gln Leu
            130                 135                 140

<210> SEQ ID NO 29
<211> LENGTH: 24
<212> TYPE: DNA
<213> ORGANISM: Artificial Sequence
<220> FEATURE:
<223> OTHER INFORMATION: Synthetic polynucleotides

<400> SEQUENCE: 29
aagacagcta tcgcgattgc agtg                                      24
```

ANTIBODIES AGAINST INFECTIOUS DISEASES

FIELD OF THE INVENTION

The invention relates to an antibody against infectious diseases. Particularly, the invention provides an antibody against alpha-enolase for diagnosis and treatment of against infections caused by *Candida*, fluconazole resistance *Candida*, *Streptococcus*, or *Staphylococcus*.

BACKGROUND OF THE INVENTION

*Candida* diseases are often chronic, difficult to treat, and carry a high mortality and morbidity despite anti-fungal therapy. *Candida* spp. are the third leading cause of infections in ICUs globally, accounting for up to 90% of all fungal infections.

The diagnosis of invasive candidiasis is difficult due to the lack of specific clinical features and to the low sensitivity of blood culture for isolation of *Candida* species, especially in patients receiving fluconazole prophylaxis. A positive blood culture for *Candida* spp. remains the gold standard for the diagnosis of candidemia. However, *Candida* spp. isolation may take too much time, thereby delaying effective antifungal therapy. *Candida albicans* is the most important human fungal pathogen. Particularly, *Candida albicans* (*C. albicans*) is an opportunistic human pathogen, which colonizes at several sites including skin, oral tissue, gastrointestinal track and vagina. *C. albicans* is also a major pathogen responsible for 50.4% of clinical candidemia. Candidemia can occur when *Candida* yeasts enter the bloodstream and is rarely seen in healthy people. In recent decades, due to the increase of patient population with defective immunological functions, Candidemia has become an important issue. Amphotericin (AmB) is a gold standard of antifungal treatment for fungi, but the severe side effect of this drug restricts its clinical application. Widespread and prolonged use of azoles has led to the rapid development of multidrug resistance (MDR), which poses a major hurdle in antifungal therapy. Several reports show that the incidence of resistance to fluconazole has risen during the last two decades.

Enolase is present in all tissues and organisms capable of glycolysis or fermentation. ENO1 was first identified as a key component of the glycolytic pathway. ENO1 is ubiquitously expressed in the cytosol and also found on the cell surface as a plaminogen-binding receptor. *Candida albicans* ENO1 null mutants exhibit altered drug susceptibility, hyphal formation, and virulence. The expression of ENO1 in the fungal pathogen *Candida albicans* is critical for cell growth. Mutations on ENO1 in *Candida albicans* inhibit cell growth in the presence of glucose. ScFv is a recombinant antibody protein, which consists of the variable regions of heavy chain (VH) and light chain (VL), combining by a linker peptide. In a previous study, anti-CaENO1 scFv antibody (CaS1) was isolated by phage display, but the interaction (epitope) of CaENO1 with CaS1 is not clear. There is a need to explore and develop a target regarding CaS1 scFv inhibition against the interaction between CaENO1 and plasminogen.

SUMMARY OF THE INVENTION

The invention provides anti-CaENO1 antibodies (CaS1) and humanized antibodies as effective diagnostic agent or therapeutic treatment against infections caused by *Candida* (preferably *Candida* spp., more preferably, *Candida. albicans, Candida tropicalis*), fluconazole resistance *Candida* (preferably fluconazole resistance *Candida* spp.), *Streptococcus*, or *Staphylococcus*.

In the invention, recombinant CaENO1 and CaS1 scFv were expressed and purified successfully. CaS1 scFv recognizes ENO1 protein of *C. albicans, S. pneumoniae, S. aureus*; particularly, CaS1 scFv binds to fluconazole resistance *C. albicans* and *C. tropicalis* from clinic and has weak cross reactivity to those of mouse and human.

The invention also provides an epitope sequence, comprising an amino acid sequence consisting of $_{283}$LYEQLISEYP$_{292}$ (SEQ ID NO:1), $_{278}$PQLADLYEQL$_{287}$ (SEQ ID NO:2), $_{240}$KGKVGIAMDV$_{249}$ (SEQ ID NO:3) or $_{278}$PQLADLYEQLISEYP$_{292}$ (SEQ ID NO:4) located in CaENO1.

The invention also found that the polyclonal IgY antibodies showed binding activity to the recombinant CaENO1 protein as well as native CaENO1 expressed by *C. albicans*, demonstrating that a strong humoral response was elicited in chicken. The complexity of antibody libraries constructed with short or long linker was $2.4 \times 10^6$ and $1.36 \times 10^7$, respectively. After a stringent screening, a dominant CaS1 scFv specifically recognized the ENO1 protein of *C. albicans* and *C. tropicalis*. In addition, CaS1 scFv binds to fluconazole resistance *C. albicans* and *C. tropicalis* from clinic. CaS1 also attenuated the growth of *C. albicans* and inhibited its adherence to oral epidermoid carcinoma cells (OECM-1). In addition, CaS1 significantly inhibited the binding of surface ENO1 of *C. albicans* to plasminogen as showed by fibrin matrix-gel degradation analysis. Noticeably, an in vivo animal test showed that CaS1 antibody prolonged the survival time of mice with candidemia. Consequently, the invention identifies a novel CaS1 scFv monoclonal antibody with specific binding activity to CaENO1. All the results together will provide great help in exploiting the therapeutic antibody drugs against the infection of *C. albicans* for clinical application.

BRIEF DESCRIPTION OF THE DRAWINGS

FIGS. 2 A and B shows analysis of anti-CaENO1 IgY antibodies using ELISA and Western blot. (A) The purified recombinant CaENO1 protein and BSA (negative control) were coated on ELISA plates, respectively. Then, blocking plates were incubated with a series diluted polyclonal IgY antibodies from pre-immunized or 7$^{th}$-immunized chicken. (B) The total cell lysates of *C. albicans* were visualized on SDS-PAGE (Lane 1). Membranes were incubated with diluted polyclonal IgY antibodies from pre-immunized (lane 2) or 7$^{th}$-immunized (lane 3) chicken, followed by HRPlabeled donkey anti-chicken IgY (1:3,000). The detected ENO1 protein expressed in cell lysates of *C. albicans* is indicated by an arrow.

FIG. 3 shows sequence alignment of VH and VL domains of scFv antibodies. Nucleotide sequences of 10 scFv-S randomly selected from the antibody libraries through 4th panning. The putative amino acid sequences were aligned with that of chicken germline gene. Sequence gaps were introduced to maximize the alignment by blank space.

FIGS. 7 (A) and (B) shows flow cytometry analysis of *C. albicans* with scFv CaS1. (A) *C. albicans* SC 5314 were cultured overnight and $10^5$ cells were added to each tube with 2 ml YPD medium. Experiment antibodies were added to each tube (1) Anti-CaENO1 IgY (100 ug) (2) Control scFv (100 ug) (3) scFv CaS1 (100 ug) (4) PBS, and cultured 2 hours at 37° C. in an incubator. Goat anti-chicken light chain (1:1500) antibody was used as detected antibody; FITC donkey anti-goat antibody (1:1000) was used as developed antibody to detect the reaction. Propidium iodide (PI) (1 ug/ml) was used to detect cell death. (B) Quantification of flow cytometry result in the panel A (*, p<0.05;**, p<0.01). Flow cytometry is represented as mean±SD of the duplicated experiment.

FIG. 9 shows the effects of CaS1 scFv on *C. albicans* growth and hyphal formation. (A) *C. albicans* were cultured in YPD medium overnight at 37° C. 108 cfu/ml of *C. albicans* was mixed with equal volume of 0.5 mg/ml anti-CaENO1 IgY, 0.5 mg/ml CaS1 scFv or 1×PBS, respectively, at room temperature for 1 hr. 1 ul of each mixture in 10× dilutions was spotted on YPD agar plate and incubated at 37° C. overnight. (B) $10^3$ cfu of *C. albicans* was mixed with PBS (control), 10 or 100 □g/ml CaS1 scFv at room temperature for 1 hr. 1 ul of each mixture was spotted on YPD agar plate and incubated at 37° C. for 5 days. The hyphal formation was observed under the microscope.

FIG. 14 (A) to (D) shows $K_D$ determination of hzCaS1 V1 and V3 scFv by ELISA. (A, C) Purified hzCaS1 V1 and V3 scFv were used to recognize recombinant CaENO1 protein. The hzCaS1 V1 and V3 scFv were used as primary antibody with series dilution. The goat anti-chicken light chain IgG was used as secondary antibody. The HRP conjugated donkey anti-goat IgG was used to decet. (B, D) OD value was calculated into percentage. The $K_D$ or 50% effective concentration ($EC_{50}$) of scFv were calculated and expressed by molarity (M). $K_D$ of hzCaS1 V1 and V3 scFv is 1.51 ug/ml=$4.6 \times 10^{-8}$ M and 2.12 ug/ml=$8.4 \times 10^{-8}$ M, respectivity. ELISA data were represented as mean±SD of the duplicated well.

Figure 15:
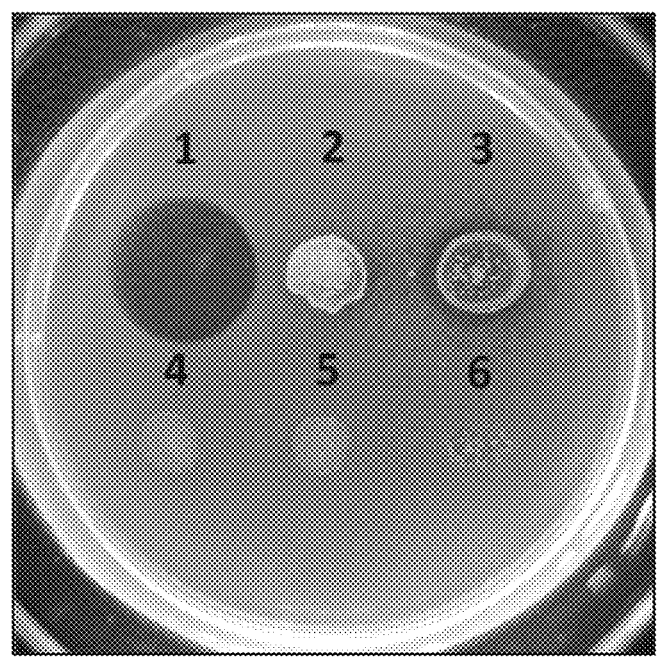

FIG. 15 shows that CaS1, hzCaS1 V1 and V3 scFv inhibits CaENO1 binding to plasminogen. CaENO1 on $Ni^+$ sepharose was treated with 100 ug hzCaS1 V1, V3 and CaS1 scFv for 1 hour, following incubating with plasminogen (20 ug) for 1 hour. Each experimental group of CaENO1 with CaS1 scFv were dropped onto gel and incubated at room temperature for 2 days to observe gel degrade result. (1) plasminogen (1 ug/ul) only. (2) CaENO1 on Ni Sepharose™ (10 ug). (3) CaENO1 on Sepharose™ (10 ug) with plasminogen (20 ug). (4-6) CaENO1 on Sepharose™ (10 ug) treated with hzCaS1 V1, V3, CaS1 scFv (100 ug) and incubated with plasminogen (20 ug).

FIG. 16 shows that epitope of CaENO1 with CaS1 scFv is close to binding site of plasminogen with CaENO1. Epitope of CaENO1 with CaS1 scFv ($_{240}$KGKV-GIAMDV$_{249}$ and $_{278}$PQLADLYEQLISEYP$_{292}$) and plasminogen binding site (the last blocking region indicated in the sequence of the figure) is indicated.

Figure 17:
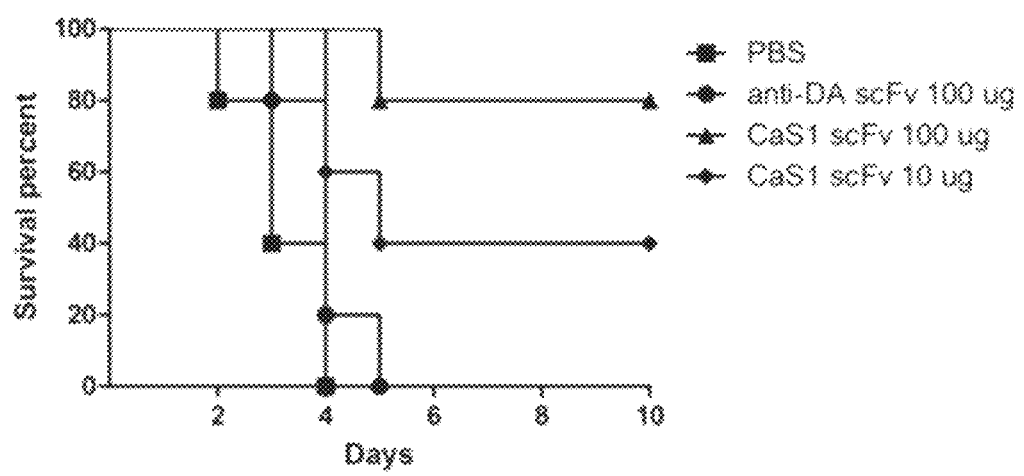

FIG. 17 shows the effect of CaS1 scFv on the survival of mice challenged with *C. albicans*. The mice were grouped and challenged with the mixture of $10^6$ of *C. albicans* containing 10 ug and 100 ug CaS1 scFv, 100 ug anti-DA scFv (unrelated scFv control) or 1×PBS, respectively. The survival of mice was monitored at 1 day intervals for 10 days. It is noticeable that CaS1 scFv antibodies provides significant protective activity against the lethal challenge of *C. albicans* in mice.

Figure 18:
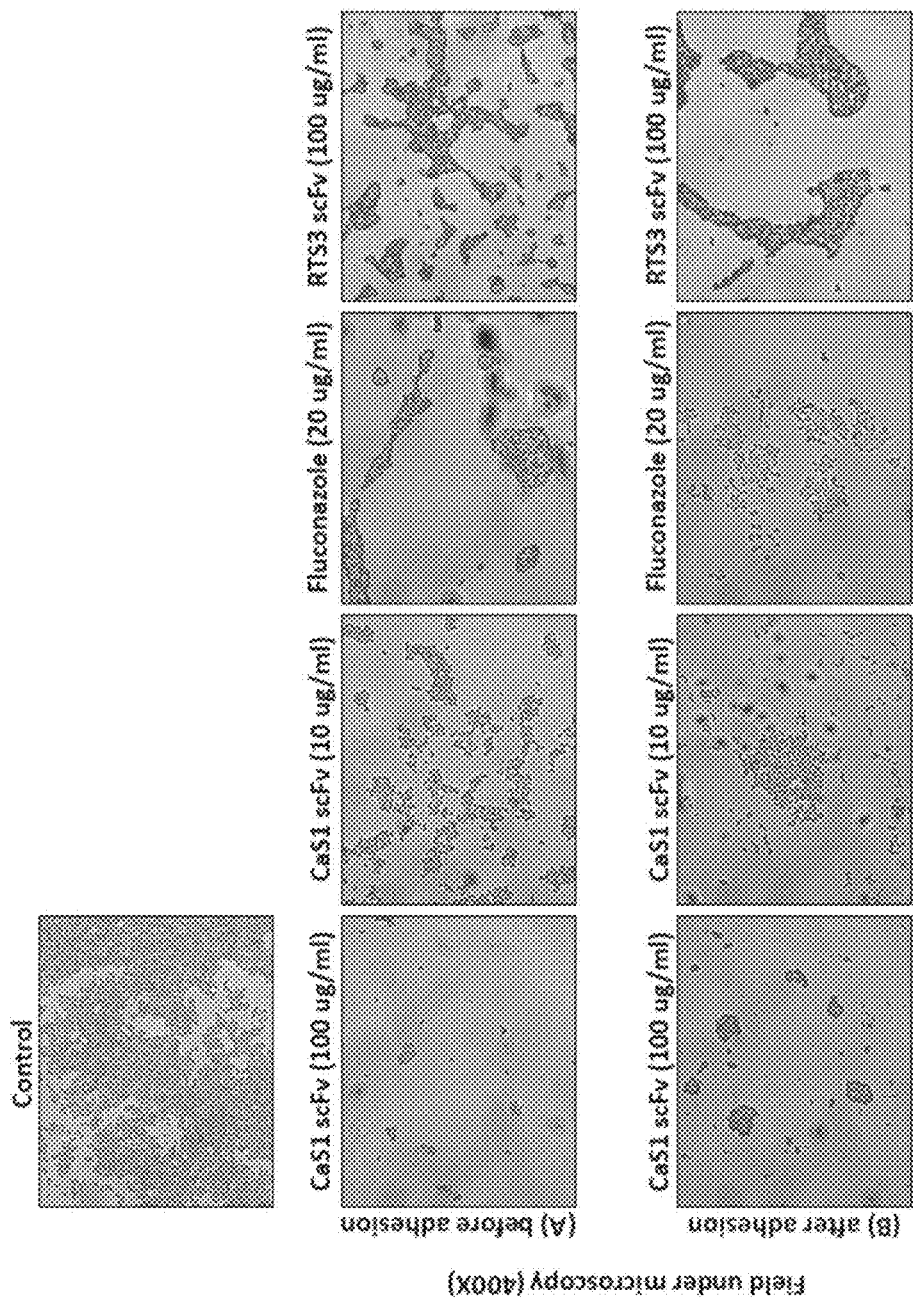

FIG. 18 shows *Candida albicans* biofilm formation inhibition assay.

DETAILED DESCRIPTION OF THE INVENTION

The invention develops an epitope of CaENO1 and anti-CaENO1 antibodies (CaS1) as an effective diagnostic agent or therapeutic treatment against infections caused by *Candida, Streptococcus* and *Staphylococcus*.

Definitions

In the description that follows, a number of terms are used for which the following definitions are provided to facilitate understanding of the claimed subject matter. Terms that are not expressly defined herein are used in accordance with their plain and ordinary meanings.

Unless otherwise specified, "a" or "an" means "one or more."

As used herein, the term "epitope" refers to the site on the antigen to which an antibody binds.

As used herein, the term "candidiasis" refers to a fungal infection due to any type of *Candida* (a type of yeast).

As used herein, the term "antibody" refers to single chain, two-chain, and multi-chain proteins and polypeptides belonging to the classes of polyclonal, monoclonal, chimeric, and humanized antibodies; it also includes synthetic and genetically engineered variants of these antibodies. "Antibody fragment" includes Fab, Fab', F(ab')$_2$, and Fv fragments, as well as any portion of an antibody having specificity toward a desired target epitope or epitopes.

As used herein, the term "polyclonal antibody" refers to an antibody which is produced among or in the presence of one or more other, non-identical antibodies. In general, polyclonal antibodies are produced from a B-lymphocyte in the presence of several other B-lymphocytes producing non-identical antibodies. Usually, polyclonal antibodies are obtained directly from an immunized animal.

As used herein, the term "monoclonal antibody" refers to an antibody obtained from a population of substantially homogeneous antibodies. In other words, a monoclonal antibody consists of a homogeneous antibody arising from the growth of a single cell clone (for example a hybridoma, a eukaryotic host cell transfected with a DNA molecule coding for the homogeneous antibody or a prokaryotic host cell transfected with a DNA molecule coding for the homogeneous antibody). These antibodies are directed against a single epitope and are therefore highly specific.

As used herein, the term "single chain Fv" or "scFv" refers to an antibody in which the heavy chain and the light chain of a traditional two chain antibody have been joined to form one chain. Typically, a linker peptide is inserted between the two chains to allow for proper folding and creation of an active binding site.

The term "linker peptide" includes reference to a peptide within an antibody binding fragment (e.g., Fv fragment) which serves to indirectly bond the variable heavy chain to the variable light chain. The linker may be a series of a single amino acid or an alternating pattern of amino acids, for example.

As used herein, the term "complementarity determining region" (CDR) refers to the non-contiguous antigen combining sites found within the variable region of both heavy and light chain polypeptides. CDRs have been described by Kabat et al., J. Biol. Chem. 252:6609-6616 (1977); Kabat et al., U.S. Dept. of Health and Human Services, "Sequences of proteins of immunological interest" (1991); by Chothia et al., J. Mol. Biol. 196:901-917 (1987); and MacCallum et al., J. Mol. Biol. 262:732-745 (1996), where the definitions include overlapping or subsets of amino acid residues when compared against each other.

As used herein, the term "humanized antibody" refers to a recombinant protein in which the CDRs from an antibody from one species; e.g., a murine or a chicken antibody, are transferred from the heavy and light variable chains of the antibody from the species into human heavy and light variable domains (framework regions). The constant domains of the antibody molecule are derived from those of a human antibody. In some cases, specific residues of the framework region of the humanized antibody, particularly those that are touching or close to the CDR sequences, may be modified, for example replaced with the corresponding residues from the original murine, rodent, subhuman primate, or other antibody. The humanized antibody may be achieved by various methods including (a) grafting only the non-human CDRs onto human framework and constant regions with or without retention of critical framework residues, or (b) transplanting the entire non-human variable domains, but "cloaking" them with a human-like section by replacement of surface residues. Such methods as are useful in practicing the present invention include that disclosed in Padlan, Mol. Immunol., 31(3):169-217 (1994).

As used herein, the term "chimeric antibody" refers to a recombinant protein that contains the variable domains of both the heavy and light antibody chains, including the complementarity determining regions (CDRs) of an antibody derived from one species, preferably a rodent antibody or a chicken antibody, more preferably a murine antibody, while the constant domains of the antibody molecule are derived from those of a human antibody.

As used herein, the term "phage display library" refers to a population of bacteriophage, each of which contains a foreign cDNA recombinantly fused in frame to a surface protein. The phage displays the foreign protein encoded by the cDNA on its surface. After replication in a bacterial host, typically *E. coli*, the phage which contain the foreign cDNA of interest are selected by the expression of the foreign protein on the phage surface.

As used herein, the term "sequence identity" in the context of two nucleic acid or polypeptide sequences includes reference to the nucleotides (or residues) in the two sequences which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers & Miller, Computer Applic. Biol. Sci. 4:11-17 (1988), e.g., as implemented in the program PC/GENE (Intelligenetics, Mountain View, Calif., USA). An indication that two peptide sequences are substantially similar is that one peptide is immunologically reactive with antibodies raised against the second peptide. Thus, a peptide is substantially similar to a second peptide, for example, where the two peptides differ only by a conservative substitution.

A "comparison window", as used herein, includes reference to a segment of about 10-20 residues in which a sequence may be compared to a reference sequence of the same number of contiguous positions after the two sequences are optimally aligned. Methods of alignment of sequences for comparison are well known in the art. Optimal alignment of sequences for comparison may be conducted by the local homology algorithm of Smith & Waterman, Adv. Appl. Math. 2:482 (1981); by the homology alignment algorithm of Needleman & Wunsch, J. Mol. Biol. 48:443 (1970); by the search for similarity method of Pearson & Lipman, Proc. Nat'l Acad. Sci. USA 85:2444 (1988); by computerized implementations of these algorithms (including, but not limited to CLUSTAL in the PC/Gene program by Intelligenetics, Mountain View, Calif., GAP, BESTFIT, BLAST, FASTA, and TFASTA in the Wisconsin Genetics Software Package, Genetics Computer Group (GCG), Madison, Wis., USA); the CLUSTAL program is well described by Higgins & Sharp, Gene 73:237-244 (1988) and Higgins & Sharp, CABIOS 5:151-153 (1989); Corpet, et al., Nucl. Acids Res. 16:10881-90 (1988); Huang, et al., Computer Applications in the Biosciences 8:155-65 (1992); and Pearson, et al., Meth. in Molec. Biol. 24:307-31 (1994).

As used herein, the term "diagnostic" or "diagnosed" means identifying the presence or nature of a pathologic condition.

As used herein, the terms "treatment," "treating," and the like, cover any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

As interchangeably used herein, the terms "individual," "subject," "host," and "patient," refer to a mammal, including, but not limited to, murines (rats, mice), non-human primates, humans, canines, felines, ungulates (e.g., equines, bovines, ovines, porcines, caprines), etc.

As used herein, the term "therapeutically effective amount" or "efficacious amount" refers to the amount of a subject anti-CaENO1 antibody that, when administered to a mammal or other subject for treating a disease, is sufficient to effect such treatment for the disease.

As used herein, the term "biological sample" encompasses a variety of sample types obtained from an individual, subject or patient that can be used in a diagnostic or monitoring assay. The definition encompasses blood and other liquid samples of biological origin, solid tissue samples such as a biopsy specimen or tissue cultures or cells derived therefrom and the progeny thereof.

Epitopes Located in *Candida albicans* ENO1 (CaENO1) and Antibodies Against *Candida* Alpha-Enolase In one aspect, the invention provides an epitope sequence, comprising an amino acid sequence consisting of $_{283}$LYEQ-LISEYP$_{292}$ (SEQ ID NO:1), $_{278}$PQLADLYEQL$_{287}$ (SEQ ID NO:2), $_{240}$KGKVGIAMDV$_{249}$ (SEQ ID NO:3) or $_{278}$PQ-LADLYEQLISEYP$_{292}$ (SEQ ID NO:4) located in CaENO1. In one embodiment, the epitope sequence comprises an amino acid sequence consisting of $_{240}$KGKVGIAMDV$_{249}$ (SEQ ID NO:3) or $_{278}$PQLADLYEQLISEYP$_{292}$ (SEQ ID NO:4) located in CaENO1.

The purified CaS1 scFv is used to recognize recombinant CaENO1 protein. The epitope region is mapped to contain 198 bp nucleotides, which deduces the following amino acid sequence (residues 235 to 300): DKAGYKGKVGIAMDVASSEFYKDGKYDLDFKNPESDPSKWLSGPQLADLYEQLISEYPIVS IEDPF (SEQ ID NO:19) (66 amino acids). To further determine the epitopic location, site directed mutagenesis is used to construct nine peptide-expressing phages according to the nucleotide sequences of 198 bp of mapped antigenic fragment. In one embodiment, CaS1 scFv antibody binds to a fragment of plasminogen spanning amino acid residues 301 to 437, which sequences are AEDDWDAWVHFFERVGDKIQIVGDDLTVTNPTRIK-TAIEKKAANALLLKVNQIGTLTESIQAANDSYAA GW-GVMVSHRSGETEDTFIADLSVGLRSGQIKTGAPAR-SERLAKLNQILRIEEEL GSEAIYAGKDFQKA (SEQ ID NO:20).

In one aspect, the present invention provides an isolated anti-CaENO1 antibody or an antigen-binding portion thereof, comprising at least one of a light chain complementarity determining region 1 (L-CDR1) of SEQ ID NO:5 or a variant having amino acid sequence with at least 80% identity to any of L-CDR1s; a light chain CDR2 (L-CDR2) of SEQ ID NO:6 or a variant having amino acid sequence with at least 80% identity to any of L-CDR2s; and a light chain CDR3 (L-CDR3) of SEQ ID NO:7 or a variant having amino acid sequence with at least 80% identity to any of L-CDR3s; and at least one of a heavy chain CDR1 (H-CDR1) of SEQ ID NO:8 or a variant having amino acid sequence with at least 80% identity to any of H-CDR1s; a heavy chain CDR2 (H-CDR2) of SEQ ID NO:9 or a variant having amino acid sequence with at least 80% identity to any of H-CDR2s; and a heavy chain CDR3 (H-CDR3) of SEQ ID NO:10 or a variant having amino acid sequence with at least 80% identity to any of H-CDR3s; such that said isolated antibody or antigen-binding portion thereof binds to CaENO1. Preferably, the sequence identity as mentioned above is at least 81%, 82%, 83%, 84%, 85%, 86%, 87%, 88%, 89%, 90%, 91%, 91%, 92%, 93%, 94%, 95%, 96%, 97%, 98% or 99%.

The amino acid sequences of the complementarity determining regions (CDRs) in heavy chains and light chains are listed in the table below.

| CDRs of Light Chain | | |
|---|---|---|
| L-CDR1 | L-CDR2 | L-CDR3 |
| SGSYG (SEQ ID NO: 5) | SNN (SEQ ID NO: 6) | GSRDSSYVGV (SEQ ID NO: 7) |

| CDRs of Heavy Chain | | |
|---|---|---|
| H-CDR1 | H-CDR2 | H-CDR3 |
| GFTFIDYG (SEQ ID NO: 8) | IGSSGSST (SEQ ID NO: 9) | AKSAGGYCVNGAGCNGGSIDA (SEQ ID NO: 10) |

The preceeding CDR sequences are determined by using the international ImMunoGeneTics information System® (http://www.imgt.org).

In some embodiments, the isolated anti-CaENO1 antibody is a monoclonal antibody, chimeric antibody, humanized antibody or human antibody.

Accordingly, the invention provides a light chain of an anti-CaENO1 scFv monoclonal antibody (CaS1) comprising an amino acid sequence consisting of the sequence: ALTQPSSVSANLGGTVKITCSGGSGSYGWYQQKS-PGSAPVTVIYSNNQRPSNIPSRFSGSPSG STGTLTITG-VQADDEAVYFCGSRDSSYVGFGAGTTLTVL (SEQ ID NO:11). The invention provides a heavy chain of an anti-CaENO1 scFv monoclonal antibody (CaS1) comprising an amino acid sequence consisting of the sequence: TVT-LDESGGGLQTPRGALSLVCKASGFTHDYGMQWV-RQAPGKGLEWVAGIGSSGSSTNYGAAVKGRATIS-RDDGQSTVRLQLNNLRAEDTGTYYCAKSAG-GYCVNGAGCNGGSIDAWG HGTEVIVSS (SEQ ID NO:12). The invention also provides an anti-CaENO1 scFv monoclonal antibody (CaS1) comprising a light chain having an amino acid sequence consisting of the sequence of SEQ ID NO:11 and a heavy chain comprising an amino acid sequence consisting of the sequence SEQ ID NO:12.

The antibody molecule can be a polyclonal or a monoclonal antibody or any other suitable type of an antibody, such as a fragment or a derivative of an antibody, a single chain variable fragment (ScFv) or a synthetic homolog of the antibody, provided that the antibody has the same binding characteristics as, or that has binding characteristics comparable to, those of the whole antibody. In some embodiments, the antibody can be recombinantly produced, e.g., produced by any suitable phage display or combinatorial methods. Various phage display and combinatorial methods for generating antibodies are known in the art (as described in, e.g., Griffths et al. (1993) EMBO J 12:725-734; Hawkins et al. (1992) J Mol Biol 226:889-896; Clackson et al. (1991) Nature 352:624-628; Gram et al. (1992) PNAS 89:3576-3580; Garrad et al. (1991) Bio/Technology 9:1373-1377; Hoogenboom et al. (1991) Nuc Acid Res 19:4133-4137; and Barbas et al. (1991) PNAS 88:7978-7982).

Antibody fragments can be produced by cleaving a whole antibody, or by expressing DNA that encodes the fragment. Fragments of antibodies may be prepared by methods described in the published literature (Lamoyi et al., J. Immunol. Methods, 56:235, 1983; Parham, J. Immunol., 131:2895, 1983). Such fragments may contain one or both of an Fab fragment and an F(ab')2 fragment. Such fragments may also contain single chain variable fragment antibodies, i.e. scFv, dibodies, or other antibody fragments.

Single chain variable fragments (scFv) are polypeptides that consist of the variable region of a heavy chain of an antibody linked to the variable region of a light chain with a short peptide linker). Thus, the scFv comprises the entire antibody-combining site. These chains may be produced in bacteria, or in eukaryotic cells.

Various techniques, such as production of chimeric or humanized antibodies, may involve procedures of antibody cloning and construction. The antigen-binding variable light chain and variable heavy chain sequences for an antibody of interest may be obtained by a variety of molecular cloning procedures, such as RT-PCR, 5'-RACE, and cDNA library screening. The variable heavy or light chain sequence genes of an antibody from a cell that expresses a murine antibody can be cloned by PCR amplification and sequencing. To confirm their authenticity, the cloned $V_L$ and $V_H$ genes can be expressed in cell culture as a chimeric antibody as described by Orlandi et al., (Proc. Natl. Acad. Sci., USA, 86: 3833 (1989)). Based on the variable heavy or light chain gene sequences, a humanized antibody can then be designed and constructed as described by Leung et al. (Mol. Immunol., 32: 1413 (1995)).

A chimeric antibody is a recombinant protein in which the variable regions of a human antibody have been replaced by the variable regions of, for example, a mouse antibody, including the complementarity-determining regions (CDRs) of the mouse antibody. Chimeric antibodies exhibit decreased immunogenicity and increased stability when administered to a subject. Methods for constructing chimeric antibodies are well known in the art (e.g., Leung et al., 1994, Hybridoma 13:469).

A chimeric monoclonal antibody may be humanized by transferring the mouse CDRs from the heavy and light variable chains of the mouse immunoglobulin into the corresponding variable domains of a human antibody. The mouse framework regions (FR) in the chimeric monoclonal antibody are also replaced with human FR sequences. To preserve the stability and antigen specificity of the humanized monoclonal, one or more human FR residues may be replaced by the mouse counterpart residues. Humanized monoclonal antibodies may be used for therapeutic treatment of subjects. Techniques for production of humanized monoclonal antibodies are well known in the art. (See, e.g., Jones et al., 1986, Nature, 321:522; Riechmann et al., Nature, 1988, 332:323; Verhoeyen et al., 1988, Science, 239:1534; Carter et al., 1992, Proc. Nat'l Acad. Sci. USA, 89:4285; Sandhu, Crit. Rev. Biotech., 1992, 12:437; Tempest et al., 1991, Biotechnology 9:266; Singer et al., J. Immun., 1993, 150:2844.)

In one embodiment, the invention provides the followings amino acids of the light chains and heavy chains of humanized antibodies.

Embodiments of Amino Acid Sequences of Light
Chains (SEQ ID NO: 13)
DIQLTQSPSSLSASVGDRVTITCRASSGSYGLGWYQQKPGKAPKRLIYSN

NSLQSGVPSRFSGSGSGTEFTLTISSLQPEDFATYYCGSRDSSYVGNTGQ

GTKVEIK (hzCaS1-V1 scFv)

(SEQ ID NO: 14)
DIQMTQSPSSLSASVGDRVTITCRASSGSYGVAWYQQKPGKAPKLLIYSN

NFLYSGVPSRFSGSGSGTDFTLTISSLQPEDFATYYCGSRDSSVGVFGQG

TKVEIK (hzCaS1-V3 scFv)

Embodiments of Amino Acid Sequences of Heavy
chains (SEQ ID NO: 15)
EVKLEESGGGLVQPGGSMKLSCAASGFTFIDYGMDWVRQSPEKGLEWVAE

IGSSGSSTHYAESVKGRFTVSRDDSKSSVYLQMNSLRAEDTGIYYCAKSA

GGYCVNGAGCNGGSIDAWGQGTLVTVSA (hzCaS1-V1 scFv)

(SEQ ID NO: 16)
EVQLVESGGGLVQPGGSLRLSCAASGFTFIDYGIHWVRQAPGKGLEWVAG

IGSSGSSTYYADSVKGRFTISADTSKNTAYLQMNSLRAEDTAVYYCAKSA

GGYCVNGAGCNGGSIDAWGQGTLVTVSS (hzCaS1-V3 scFv)

In some embodiments, the invention provides alight chain comprising an amino acid sequence having a sequence selected from the group consisting of those as set forth in SEQ ID NOs:13 to 14.

In some embodiments, the invention provides a heavy chain comprising an amino acid sequence having a sequence selected from the group consisting of those as set forth in SEQ ID NOs:15 to 16.

In further embodiments, the invention comprises a humanized antibody, comprising (i) alight chain having an amino acid sequence as set forth in the sequence selected from the group consisting of SEQ ID NOs:13 to 14 or a variant having at least 80% identity to any of SEQ ID NOs:13 to 14, and (ii) a heavy chain having an amino acid sequence as set forth in the sequence selected from the group consisting of SEQ ID NOs:15 to 16 or a variant having at least 80% identity to any of SEQ ID NOs:15 to 16. Preferably, the sequence identity as mentioned above is at least 90%, 91%, 91%, 92%, 93%, 94%, 95%, 96%, 97%, 98% or 99%.

In a preferred embodiment, the humanized antibody comprises (i) a light chain having an amino acid sequence as set forth in SEQ ID NO:13 and (ii) a heavy chain having an amino acid sequence as set forth in SEQ ID NO:15 (hzCaS1-V1). In another preferred embodiment, the humanized antibody comprises (i) a light chain having an amino acid sequence as set forth in SEQ ID NO:14 and (ii) a heavy chain having an amino acid sequence as set forth in SEQ ID NO:16 (hzCaS1-V3).

In addition to recombinant methods, the antibodies and variants thereof that are disclosed herein can also be constructed in whole or in part using standard peptide synthesis. Solid phase synthesis of the polypeptides can be accomplished by attaching the C-terminal amino acid of the sequence to an insoluble support followed by sequential addition of the remaining amino acids in the sequence. Techniques for solid phase peptide synthesis are described by Barany & Merrifield, The Peptides: Analysis, Synthesis, Biology. Vol. 2: Special Methods in Peptide Synthesis, Part A. pp. 3-284; Merrifield et al., J. Am. Chem. Soc. 85:2149-2156, 1963, and Stewart et al., Solid Phase Peptide Synthesis, 2nd ed., Pierce Chem. Co., Rockford, Ill., 1984. Proteins of greater length may be synthesized by condensation of the amino and carboxyl termini of shorter fragments.

Compositions and Methods of Administrations

Certain embodiments relate to a pharmaceutical composition comprising an epitope 20 of the invention or an antibody against *Candida* alpha-enolase of the invention and a pharmaceutically acceptable carrier or excipient. By "pharmaceutically acceptable carrier" is intended, but not limited thereto, a non-toxic solid, semisolid or liquid filler, diluent, encapsulating material or formulation auxiliary of any type known to persons skilled in the art. Diluents, such as polyols, polyethylene glycol and dextrans, may be used to increase the biological half-life of the conjugate.

The pharmaceutical compositions of the present invention can be formulated according to conventional methods (for example, Remington's Pharmaceutical Science, latest edition, Mark Publishing Company, Easton, U.S.A.), and may also contain pharmaceutically acceptable carriers and additives. Examples include, but are not limited to, surfactants, excipients, coloring agents, flavoring agents, preservatives, stabilizers, buffers, suspension agents, isotonic agents, binders, disintegrants, lubricants, fluidity promoting agents, and corrigents, and other commonly used carriers can be suitably used. Specific examples of the carriers include light anhydrous silicic acid, lactose, crystalline cellulose, mannitol, starch, carmellose calcium, carmellose sodium, hydroxypropyl cellulose, hydroxypropyl methylcellulose, polyvinylacetal diethylaminoacetate, polyvinylpyrrolidone, gelatin, medium-chain triglyceride, polyoxyethylene hardened castor oil 60, saccharose, carboxymethyl cellulose, corn starch, inorganic salt, and such.

The invention also provide methods for inhibition of *Candida*, *Streptococcus* and *Staphylococcus* growth and treatment of infection caused thereby.

One embodiment is directed to a method for inhibition of *Candida*, *Streptococcus* or *Staphylococcus* growth and treatment of infection caused thereby in a subject, comprising administering an antibody against alpha-enolase of the invention to the subject. Accordingly, also provided is the use of an antibody against alpha-enolase of the invention in the manufacture of a medicament for inhibition of *Candida*, *Streptococcus* or *Staphylococcus* growth or treatment of infection caused thereby in a subject.

Another embodiment is directed to a method for prevention of growth or infection caused by *Candida*, *Streptococcus* or *Staphylococcus* in a subject, comprising administering an epitope of the invention to the subject. Accordingly, also provided is the use of epitope of the invention in the manufacture of a medicament for prevention of growth or infection caused by *Candida*, *Streptococcus* or *Staphylococcus* in a subject.

In some embodiments, the *Candida* is *C. albicans*, *Candida tropicalis*, and *Candida glabrate*, *C. albicans*, the *Streptococcus* is *S. pneumoniae* and the *Staphylococcus* is *S. aureus*.

Another embodiment is directed to a method for treating candidiasis in a subject comprising administering an antibody against alpha-enolase of the invention to the subject. Accordingly, also provided is the use of an antibody against alpha-enolase in the invention in the manufacture of a medicament for treatment of candidiasis in a subject. Preferably, the candidiasis disease is invasive candidiasis, antibiotic candidiasis, dysbiosis of the gut mycobiota, onychomycosis, cutaneous candidiasis, or mucosal candidiasis.

Another embodiment is directed to a method for inhibition of fluconazole-resistance *Candida* growth or treatment of infection caused thereby in a subject, comprising administering an antibody against alpha-enolase of the invention to the subject. Accordingly, also provided is the use of an antibody against alpha-enolase in the invention in the manufacture of a medicament for inhibition of fluconazole-resistance *Candida* spp. growth or treatment of infection caused thereby in a subject. Preferably, the fluconazole-resistance *Candida* is *Candida* spp.; more preferably, the fluconazole-resistance *Candida* is fluconazole resistance *C. albicans* or *C. tropicalis*.

Another further embodiment is to provide a method for inhibition of biofilm formation caused by *Candida*, comprising administering an antibody against alpha-enolase of the invention to the subject. Accordingly, also provided is the use of an antibody against alpha-enolase in the invention in the manufacture of a medicament for inhibition of biofilm formation caused by *Candida*. Preferably, the *Candida* is *C. albicans*, *Candida tropicalis* and *Candida* glabrate, *C. albicans*. Biofilms are one of the main reasons why a *Candida* overgrowth is so hard to defeat. A longstanding *Candida* overgrowth has had plenty of time to create biofilms, and these are very resistant to many treatments. The longer the biofilm has had to develop, the more resistant it will be to antifungal treatments. This is why using antifungal drugs alone is often not enough to inhibit a *Candida* overgrowth. Surprisingly, the invention found that the antibodies of the invention can effectively inhibit *Candida* biofilm formation.

The above methods also comprise administering the antibody against alpha-enolase of the invention concomitantly with or subsequent to other standard therapies as described in updated guidelines published in March 2009 by the Infectious Disease Society of America (IDSA) (Pappas P G, Kauffman C A, Andes D, Benjamin D K Jr, Calandra T F, Edwards J E Jr, et al. Clinical practice guidelines for the management of candidiasis: 2009 update by the Infectious Diseases Society of America. *Clin Infect Dis*. 2009 Mar. 1. 48(5):503-35).

In preferred embodiments, the subject is a mammal. Exemplary mammals include human, pig, sheep, goat, horse, mouse, dog, cat, cow, etc. Diseases that may be treated with the antibody or a pharmaceutical composition thereof include candidiasis. Examples of candidiasis include but are not limited to invasive candidiasis, antibiotic candidiasis, dysbiosis of the gut mycobiota, onychomycosis, cutaneous candidiasis, and mucosal candidiasis.

The antibody against alpha-enolase as disclosed herein or the pharmaceutical composition thereof may be administered intravenously, topically, intra-peritoneally, intra-arterially, intra-thecally, intra-vesically, or intratumorally. One of ordinary skill will appreciate that effective amounts of the antibody against alpha-enolase or its composition can be determined empirically. It will be understood that, when administered to a human patient, the total daily usage of the antibody against alpha-enolase or its composition will be decided by the attending physician within the scope of sound medical judgment. The specific therapeutically effective dose level for any particular patient will depend upon a variety of factors: the type and degree of the cellular response to be achieved; activity of the specific the antibody against alpha-enolase or its composition employed; the age, body weight, general health, sex and diet of the patient; the time of administration, route of administration, and rate of excretion of the antibody against alpha-enolase or its composition; the duration of the treatment; drugs used in combination or coincidental with the antibody against alpha-enolase or its composition; and like factors well known in the medical arts.

Each of the above identified compositions and methods of treatment may additionally include an additional anti-*Candida*, anti-*Streptococcus* or anti-*Staphylococcus* drug. In some embodiments, anti-*Candida* drugs suitable for use with the present invention include, but are not limited to, fluconazole, itraconazole, posaconazole, echinocandins caspofungin, micafungin, anidulafungin, voriconazole, lipid formulations of amphotericin B, Ketoconazole, clotrimazole, econazole, ciclopirox, miconazole, ketoconazole and nystatin. In the method of treatment, the antibody against alpha-enolase of the invention can be administered concurrently, subsequently or separately with the additional one or more anti-*Candida*, anti-*Streptococcus* or anti-*Staphylococcus* drugs.

Diagnosis of *Candida*, *Streptococcus* or *Staphylococcus* Infection

The present invention surprisingly found that anti-CaENO1 antibodies (CaS1) are an effective diagnostic agent or therapeutic treatment against *Candida*, *Streptococcus* or *Staphylococcus* infection. Accordingly, in another aspect, the present invention provides a method for diagnosing *Candida*, *Streptococcus* or *Staphylococcus* infection in a biological sample of a subject, comprising contacting an anti-CaENO1 antibody of the invention with the biological sample and detecting the binding of the anti-CaENO1 antibody to an epitope of CaENO1 of the invention wherein the presence of the binding indicates that the subject is suspected of suffering from *Candida*, *Streptococcus* or *Staphylococcus* infection. Alternatively, the present invention provides a method for diagnosing *Candida*, *Streptococcus* or *Staphylococcus* infection in a biological sample of a subject, comprising contacting an epitope sequence of the invention with the biological sample and detecting the binding of the epitope sequence of the invention to an anti-CaENO1 antibody wherein the presence of the binding indicates that the subject is suspected of suffering from *Candida* infection.

In the present invention, detection includes quantitative and qualitative detection. Examples of qualitative detection include the following: simple detection of the presence or absence of the binding of the anti-CaENO1 antibody to an epitope of CaENO1 of the invention; determination of whether or not the binding is present above a certain amount; and comparison of the amount of the binding with that of other samples (for example, a control sample).

Biological samples used in the diagnostic methods of the present invention are not particularly limited as long as they are samples that may contain a CaENO1 protein. Specifically, samples collected from the body of an organism such as a mammal are preferred. Samples collected from humans are more preferred. Specific examples of the test samples include blood, interstitial fluid, plasma, cerebrospinal fluid, synovial fluid, pleural fluid, serum, lymphatic fluid, saliva, urine, tissue and ascites.

In the present invention, "control" refers to samples serving as a standard for comparison, including negative controls and biological samples from healthy subjects. Negative control can be obtained by collecting biological samples from healthy subjects and mixing them as necessary. The level of binding of the anti-CaENO1 antibody to an epitope of CaENO1 in a control can be detected in parallel with the binding level in the biological sample of a subject. Alternatively, by detecting the binding level in biological samples of many healthy subjects in advance, a standard expression level in healthy subjects can be determined statistically.

In the present invention, the binding level can be determined by any method. Methods for detecting the binding in a test sample are not particularly limited. An immunological method using an anti-CaENO1 antibody for detection is provided, such as radioimmunoassay (RIA); enzyme immunoassay (EIA); fluorescence immunoassay (FIA); luminescence immunoassay (LIA); immunoprecipitation (IP); turbidimetric immunoassay (TIA); Western blotting (WB); immunohistochemical (IHC) method; and single radial immunodiffusion (SRID).

The present invention also provides diagnostic agents or kits for diagnosing a *Candida*, *Streptococcus* or *Staphylococcus* infection, comprising a diagnostic agent for detecting the binding of the anti-CaENO1 antibody to a CaENO1 in a test sample. The diagnostic agents of the present invention comprise at least a *Candida* infection.

Kits for diagnosing cancer can be produced by combining the agents for diagnosing a *Candida* infection with another element used for detecting the anti-CaENO1 antibody. More specifically, the present invention relates to kits for diagnosing a *Candida*, *Streptococcus* or *Staphylococcus* infection which comprise an anti-CaENO1 antibody that binds to CaENO1 and a reagent for detecting binding between the antibody and CaENO1. In addition, instructions that describe the measurement operation can be attached to the kits of the present invention.

EXAMPLES

Materials and Methods

Expression and Purification of his-CaENO1 Protein

Briefly, *C. albicans* alpha-enolase genes were constructed in pQE30 plasmids to form pQE30-CaENO1 vector, and then the resulting vectors were transformed with *E. coli* BL21 cells. The bacterial culture was grown in 10 ml LB medium containing ampicillin (50 g/ml) at 37° C. overnight, diluted 10-fold in the same LB medium and further grown until the $OD_{600}$ reached between 0.6 and 1.0. To induce CaENO1 protein expression, isopropyl-β-D-thiogalactopyranoside (IPTG) was added to a final concentration of 0.5 mM in the culture. The cell pellet was resuspended in 2 ml of 1×PBS containing 1% Triton x–100 and lysed by three cycles of freezing (–70° C.) and thawing (37° C.). After centrifugation, the resulting cellular lysate was incubated with a $Ni^{2+}$-charged resin column to purify His-CaENO1 protein according to the manufacturer's instruction (GE Healthcare Bio-Sciences AB, Sweden). ENO1 from human, mouse, *S. pneumonia*, *S. aureus* were expressed and purified in the same way.

Animal Immunization

Female white leghorn (*Gallus domesticus*) chickens were immunized with 50 Hg of purified His-CaENO1 in an equal volume of Freund's complete adjuvant (Sigma, USA) by intramuscular injection. Three additional immunizations with His-CaENO1 in Freund's incomplete adjuvant were performed at intervals of 7 days. After each immunization, polyclonal IgY antibodies in egg yolk were partially purified and titrated by an enzyme-linked immunosorbent assay (ELISA) to determine the presence of humoral anti-his-CaENO1 immune response. The IgY antibodies were purified from the yolk separated from the egg white using 10% Dextran sulphate as described previously (Akita E M, Nakai S. Comparison of four purification methods for the production of immunoglobulins from eggs laid by hens immunized with an enterotoxigenic *E. coli* strain. J Immunol Methods 1993; 160: 207-14; Akita E M, Nakai S. Production and purification of Fab' fragments from chicken egg yolk immunoglobulin Y (IgY). J Immunol Methods 1993; 162: 155-64). The purified IgY antibodies were dissolved in 5 ml of TBS containing 0.05% sodium azide and stored at –20° C.

Construction of scFv Antibody Libraries and Panning

The antibody libraries were established based on the previous report (Andris-Widhopf J, Rader C, Steinberger P et al. *Methods for the generation of chicken monoclonal antibody fragments by phage display. J Immunol Methods* 2000; 242: 159-81). Briefly, spleens harvested from chickens following the final immunization were placed immediately in Trizol (Gibco BRL., USA) for homogenization. Ten g of total RNA was reversely transcribed into the first-strand cDNA using a SuperScript RT kit (Invitrogen, USA). After amplification using chicken-specific primers, PCR products of heavy and light chain variable (VH and VL) regions were subjected to a second round of PCR to form full-length scFv fragments with a short or long linker, which were further digested with SfiI and cloned into the pComb3X vector. Recombinant phage DNAs were transformed into *E. coli* ER2738 strain by electroporation (MicroPulser from Bio-Rad). The production of recombinant phages was initiated by the addition of wild-type VCS-M13 helper phage, which were subsequently precipitated with 4% polyethylene glycol 8000 and 3% NaCl (w/v), and finally re-suspended in 1× phosphate-buffered saline (PBS) containing 1% bovine serum albumin (BSA). Then, $10^{11}$ plaque-forming units (pfu) of recombinant phages in the scFv antibody libraries were added to wells pre-coated with purified His-CaENO1 protein (0.5 μg/well) and incubated at 37° C. for 2 hrs. After the unbound phages were removed, bound phages were eluted with 0.1 M HCl/glycine (pH 2.2)/0.1% BSA, neutralized with 2 M Tris base buffer and used to infect the *E. coli* ER2738 strain. The amplified phages were precipitated and recovered as described above for the next round of selection. After $4^{th}$ biopanning, total phagemid DNA from *E. coli* ER2738 was purified and transformed into *E. coli* TOP10F'. A panel of randomly selected clones was cultured overnight, diluted 100× in super broth containing 1 mM MgCl2 and ampicillin (50 μg/ml) and further grown for 8 hr. After induction with 1 mM isopropyl-β-D-thiogalactopyranoside (IPTG) overnight, the bacteria were harvested through centrifugation, resuspended in histidine (His)-binding buffer (20 mM sodium phosphate, 0.5 M NaCl, 20 mM imidazole, pH7.4), and lysed by 3 cycles of freezing, thawing/sonication. The scFv antibodies were purified using $Ni^{2+}$-charged Sepharose (GE Healthcare Bio-Sciences AB, Sweden) according to the manufacturer's instructions. The purified scFv antibodies were further concentrated in 1×PBS using Amicon Ultra-4 Centrifugal Filter Devices (Merck Millipore, Germany) and examined for their binding or neutralizing capability against *C. albicans*.

*C. albicans* Growth and Hyphal Formation

To determine the effect of scFv antibodies on the cell growth and hyphal formation, anti-CaENO1 IgY (0.5 mg/ml) or CaS1 scFv (0.5 mg/ml) or PBS were pre-incubated with *C. albicans* (1×$10^6$ cfu) for 1 hr at 37° C. After incubation, 1 ul of each mixture in 10-fold dilutions was spotted on YPD agar plate and incubated at 37° C. overnight. $10^3$ cfu of *C. albicans* was mixed with 0 (1×PBS control), 10 or 100 g/ml CaS1 scFv at room temperature for 1 hr. Thereafter, 1 ul of each mixture was spotted on YPD agar plate and incubated at 37° C. for 5 days. *Candida* spp. strains.

*C. albicans* (SC 5314), *C. kruesi* (clinical isolate), *C. tropicalis* (BCRC 20520), *C. parapsilosis* (BCRC 20515) and *C. glabrate* (BCRC 20586) were kindly provided by Dr. Ching-Hua Su from Taipei Medical University, Taipei, Taiwan. *C. albicans* (CA6-17, CA7-26, CA7-3, CA10-50, CA7-30, CA10-65), *C. tropicalis* (CT11-52, CT6-29, CT6-50, CT12-54), *C. glabrate* (CG5-8, CG8-11, CG7-37, CG5-66), and *C. parapsilosis* (CP8-20, CP12-37, CP6-20, CP7-17, CP8-48) were kindly provided by Department of Laboratory Medicine, Wan Fang Hospital, Taipei Medical University, Taipei, Taiwan. *Candida* species were cultured in YPD medium and their identities were confirmed by CHROMagar *Candida* plate (CHROMagar, Paris, France). MIC test strips were used and MIC was read at 80% inhibition as recommended by the manufacturer.

Western Blotting

To detect the presence of ENO1 proteins, the purified recombinant ENO1 protein or cell lysates of five *Candida* spp were subjected to SDS-PAGE analysis, transferred onto nitrocellulose membranes (Amersham Biosciences, UK) and then blocked with 5% skim milk in TBST for 1 hr. The anti-CaENO1 IgY from chicken after $7^{th}$ immunization (1:3,000) or purified CaS1 scFv antibody (1 µg/ml) were added and incubated for 1 hr at room temperature. After vigorous washings, horseradish peroxidase (HRP)-conjugated polyclonal donkey anti-chicken IgY antibodies (1:3,000) (Bethyl Laboratories, Montgomery, Tex., USA) were added and incubated for an additional 1 hr for detecting the bound IgY antibodies. However, goat anti-chicken light chain antibodies (1:3,000) (Bethyl Laboratories, Montgomery, Tex., USA), followed by HRP-conjugated donkey anti-goat IgG antibodies (Jackson ImmunoResearch, USA) were used for detecting the bound scFv antibodies. After washings as above, the membranes were developed with diaminobenzidine (DAB) or ECL substrate. The ImageQuant LAS4500 was used for ECL intensity detection.

ELISA and Competitive ELISA

To examine their binding reactivity, a series of diluted IgY antibodies (500-256,000-fold) purified from chicken after $7^{th}$ immunization or the recombinant CaS1 scFv antibodies (40-0.078 µg/ml) were incubated with the purified CaENO1 (10 µg/ml) immobilized on ELISA plate wells. After vigorous washings, the bound IgY antibodies were detected by adding HRP-conjugated polyclonal donkey anti-chicken IgY antibodies (1:3,000) (Bethyl Laboratories, Montgomery, Tex., USA) while the bound CaS1 scFv antibodies were detected by goat anti-chicken light chain antibodies (1:3,000) (Bethyl Laboratories, Montgomery, Tex., USA), followed by HRP-conjugated donkey anti-goat IgG antibodies (Jackson ImmunoResearch, USA). After washing as above, a tetramethylbenzidine (TMB) substrate solution (Sigma, USA) was added to the wells for color development. The reaction was stopped with 1 N HCl and optical density was measured at 450 nm using an ELISA plate reader (BioTek Synergy HT). Dissociate constant ($K_D$) was calculated according to the equation, grams/molecular weight (Da)× volume $(L)^{-1}$.

For the competitive ELISA, the procedure described above was performed except a series of diluted CaENO1 proteins (50-0.097 µg/ml) were first mixed with equal volume of CaS1 scFv antibodies (1 µg/ml) for 1 hr and added to the plates for detecting the binding specificity. The ELISA tests were carried out in the duplicated wells for each sample. ELISA data were presented as mean±SD of the duplicated experiments.

Fibrin Matrix-Gel Degradation Analysis

The matrix gel was prepared for fibrinolysis activity detection[33]. *C. albicans* ($10^6$ cells) were washed and incubated with or without CaS1scFv (10 and 100 g) at 37° C. for 1 hr. After incubation, cells were washed and incubated with plasminogen (10 µg) for 30 min. The mixtures were washed with PBS to remove free plasminogen. The resulting cell pellets were placed in a matrix gel that contained 1.25% low-melting-temperature agarose, thrombin (0.05 U/ml, Sigma) and fibrinogen (2 mg/ml, Sigma). The gel was incubated in a humidified chamber at 37° C. for 10-14 hrs until the appearance of clear spots indicated the presence of fibrinolysis activity.

Adhesion Assay

Cell adhesion assay was performed using human oral epidermal cells (OECM-1) (XXX). *C. albicans* ($1 \times 10^6$ cfu) were pre-incubated with CaS1 scFv antibodies (50 or 100 g) at 37° C. for 1 hr. After incubation, the mixtures were two-fold diluted and added onto $10^4$ OECM-1 cells cultured in 96-well plates. The plates were further incubated at 4° C. for 2 hrs. After being washed three times with 1×PBS, the plates were fixed with 10% formaldehyde. After being washed as above, the wells were blocked with skim milk for 1 hr. Thereafter, rabbit anti-*C. albicans* antibodies (1:3,000, Bethyl, USA) were added and incubated for another 1 hr, followed by adding the HRP-conjugated anti-rabbit antibodies (1:3,000, Bethyl, USA). Washings as above were always carried out between steps. TMB was used for color development, which was stopped with 1 N HCl. The intensity of the color was measured at 450 nm on an ELISA plate reader.

Mouse Model of *C. albicans* Infection

A total of 20 ICR female mice (purchased from National Laboratory Animal Center, Taiwan) weighing about 30 g were randomly grouped with 5 mice in each group. *C. albicans* were grown overnight and washed in normal saline. Four groups of mice were treated through the lateral tail vein with the following preparations: (i) 1×PBS alone; (ii) $1 \times 10^6$ cfu of *C. albicans* cells pre-incubated with 50 µg of CaS1; (iii) $1 \times 10^6$ cfu of *C. albicans* cells pre-incubated with 100 µg of CaS1; (iv) $1 \times 10^6$ cfu of *C. albicans* cells pre-incubated with anti-CaENO1 IgY. Mice were monitored for survival at 1 day intervals for 10 days. All treatments and handling of mice were carried out according to animal experimental protocols approved by the Institutional Animal Care and Use Committee of Taipei Medical University.

Example 1 Expression and Purification of Fusion Protein of His-*C. albicans* Alpha-Enoloase (his-CaENO1)

*C. albicans* alpha-enolase genes were constructed in pQE30 plasmids to form pQE30-CaENO1 vector and then the resulting vectors were transformed with *E. coli* BL21 cells. The expression of the cells were was induced with IPTG at a concentrations 1.0 mM, 0.5 mM and 0.1 mM for 4 hours, 5 hours, 8 hours and overnight. It was found that the expressed protein hads a molecular weight at of about 49 kDa by SDS-PAGE (FIG. 1A) and Western blot analysis (FIG. 1B).

*C. albicans* alpha-enolase genes were constructed in pQE30 plasmids to form pQE30-CaENO1 vector and then the resulting vectors were transformed with *E. coli* BL21 cells. The expression of the cells were was induced with IPTG at a concentrations 1.0 mM, 0.5 mM and 0.1 mM for 4 hours, 5 hours, 8 hours and overnight. It was found that the expressed protein hads a molecular weight at of about 49 kDa by SDS-PAGE and Western blot analysis. To confirm that the expressed protein mentioned above is the desired CaENO1 protein, the protein obtained in Example 1 was purified with Ni Sepharose™ High Performance, the purified protein was analyzed by SDS-PAGE and a protein with 49 kDa was confirmed as His-CaENO1 (FIG. 1C).

Example 2 Binding Assay of his-CaENO1 IgY Polyclonal Antibody to Antigen his-CaENO1

50 µg of the purified His-CaENO1 protein of Example 1 was administered to chickens to produce anti-his-CaENO1 IgY polyclonal antibodies. The polyclonal antibodies were purified from eggs by SDS-PAGE and Western blot analysis. The binding ability of the purified antibodies was assayed by Western blot and enzyme-linked immunosorbent assay (ELISA). In the ELISA assay, BSA was used as negative control, mouse anti-his IgG was used as the first antibody and HRP rabbit anti-mouse IgG was used as the second antibody. After the Western blot analysis, anti-his-CaENO1 IgY polyclonal antibodies specifically binding to His-CaENO1 were produced after immunization three times and its binding ability increased with each round of immunization.

Example 3 Binding Activity of Chicken Anti-CaENO1 IgY, Anti-CaENO1 Library Construction and Panning The humoral immune response of chicken anti-CaENO1 IgY was identified by ELISA and Western blot (FIG. 2 B). As compared to pre-immune serum and un-related BSA protein, IgY after $7^{th}$-immunization (from 500-256000-fold dilution) recognized CaENO1. (FIG. 2 A)

Two libraries with short linker and long linker were constructed as shown in Table 1. The sizes for short and long linker libraries were estimated to be $2.4 \times 10^6$ and $1.36 \times 10^7$, respectively. The elution titer after each panning were shown (Table 1). After four rounds of panning, the CaENO1 binding phage variants were greatly enriched. These results suggested the non-specific binding phage was removed throughout the panning process and the clones with specific binding affinity were enriched. The sequences were confirmed to belong to chicken immunoglobulin germline gene. The short linker with highest binding activity to CaENO1 was identified. This anti-CaENO1 scFv monoclonal antibody was named CaS1.

found that the antibodies in the ten clones have the same sequences in light chain and heavy chain (FIG. 3).

Example 4 Expression and Purification of CaS1 scFv

Figure 4:
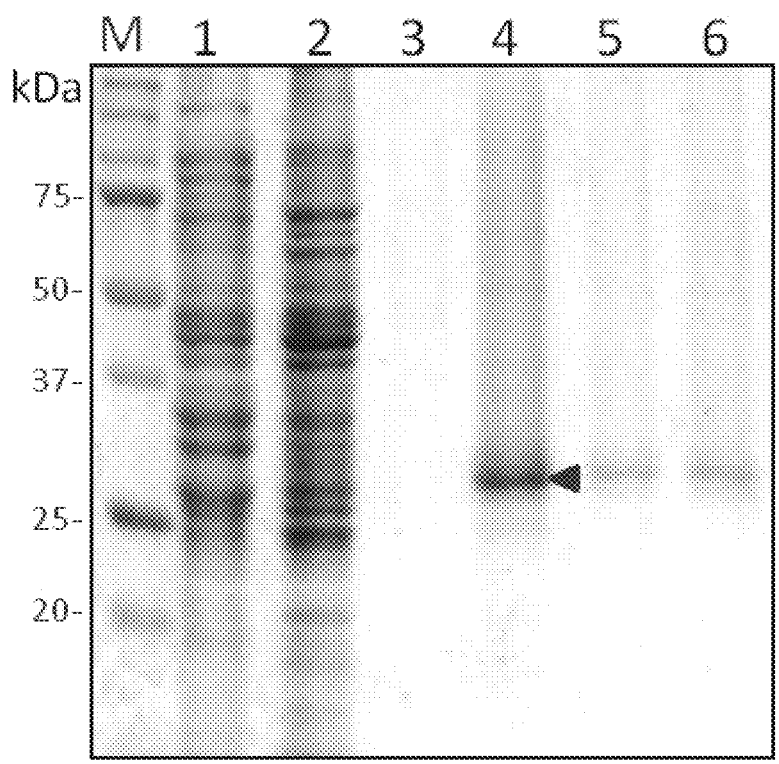
FIG. 4 shows the expression and purification of CaS1 scFv. After expression and sonication, $Ni^+$ sepharose was used to purify CaS1 scFv. The Coomassie blue was used to stain. Lane 1: total cell lysate of CaS1 scFv clone after expression. Lane 2: supernatant after $Ni^+$ sepharose binding. Lane 3: collection of first time washing buffer. Lane 4: collection of elution buffer. Lane 5: collection of second times elution buffer. Lane 6: $Ni^+$ sepharose after elution. The arrow denoted CaS1 scFv molecular weight about 25 kDa.

Total phagemid DNA from the last biopanning was transformed into TOP10F' E. coli to analyze individual scFv. The colony containing scFv gene fragment was selected and cultured in 10 mL LB (Lauria-Bertani) broth (50 µg/mL Ampicillin) with shaking at 37° C. overnight; then, the culture was transferred to another 100 mL LB (with 50 µg/mL Ampicillin) until $OD_{600}$ reached between 0.4 to 0.8. Thereafter, the resulting culture was incubated with 0.5 mM IPTG for 6-8 hours to express the His-tagged CaS1 scFv protein. Then, the culture was subjected to centrifugation and the supernatant was discarded, and the pellet was resuspended with 1 mL of His-binding buffer (20 mM sodium phosphate, 0.5 M NaCl, 20 mM imidazole, pH 7.4). The E. coli cells were disrupted with sonication; then, the sample was subjected to 3000 g centrifugation for 5 minutes. Next, the CaS1 scFv fusion protein in the supernatant was purified by Ni Sepharose™ High Performance (GE healthcare Life science, USA) as suggested by the manufacturer. In brief, the sample supernatant was added to the Sepharose, mixed for 1 hour and subjected to 1000 g centrifugation for 5 minutes. The supernatant was discarded. The Sepharose was washed with 1 mL His-binding buffer 2 times to get wash 1 and wash 2. 500 µL of His-elution buffer was added to the Sepharose and mixed for 1 hour. The Sepharose was subjected to 1000 g centrifugation for 5 minutes and the supernatant (the elution 1) was collected. The above steps were repeated to get elution 2. Elutions 1 and 2 contain the purified His-CaS1 scFv. Finally, the Sepharose was resuspended in 50 µL of His-binding buffer. Fractions of binding supernatant, wash 1, wash 2, elution 1, elution 2 and the Sepharose were analyzed by 12% SDS PAGE (FIG. 4).

Example 5 $K_D$ Determination of CaS1 scFv by ELISA and Competitive ELISA 0.25 µg of His-CaENO1 was added to each well of a 96 half area plate, and the plate was incubated at 37° C. for 1 hour to allow the adsorption of the proteins to the bottom of the wells. The proteins were discarded and 5% skimmed

TABLE 1

The anti-CaENO1 library size and eluted phage titers after each round of panning.

| Library | Linker length* | Library size | Eluted phage titers after each round of panning | | | |
|---|---|---|---|---|---|---|
| | | | $1^{st}$ | $2^{nd}$ | $3^{rd}$ | $4^{th}$ |
| CaENO1-S | 7 aa | $2.4 \times 10^6$ | $9.6 \times 10^4$ | $9.0 \times 10^5$ | $7.2 \times 10^5$ | $3.0 \times 10^6$ |
| CaENO1-L | 18 aa | $1.36 \times 10^7$ | $2.75 \times 10^5$ | $1.2 \times 10^6$ | $1.32 \times 10^6$ | $1.2 \times 10^5$ |

*Linker length of 7 aa and 18 aa are GQSSRSS (SEQ ID NO: 17) and GQSSRSSGGGGSSGGGGS (SEQ ID NO: 18), respectively.

Example 3 Gene Sequencing of scFv Antibody

Figure 5:
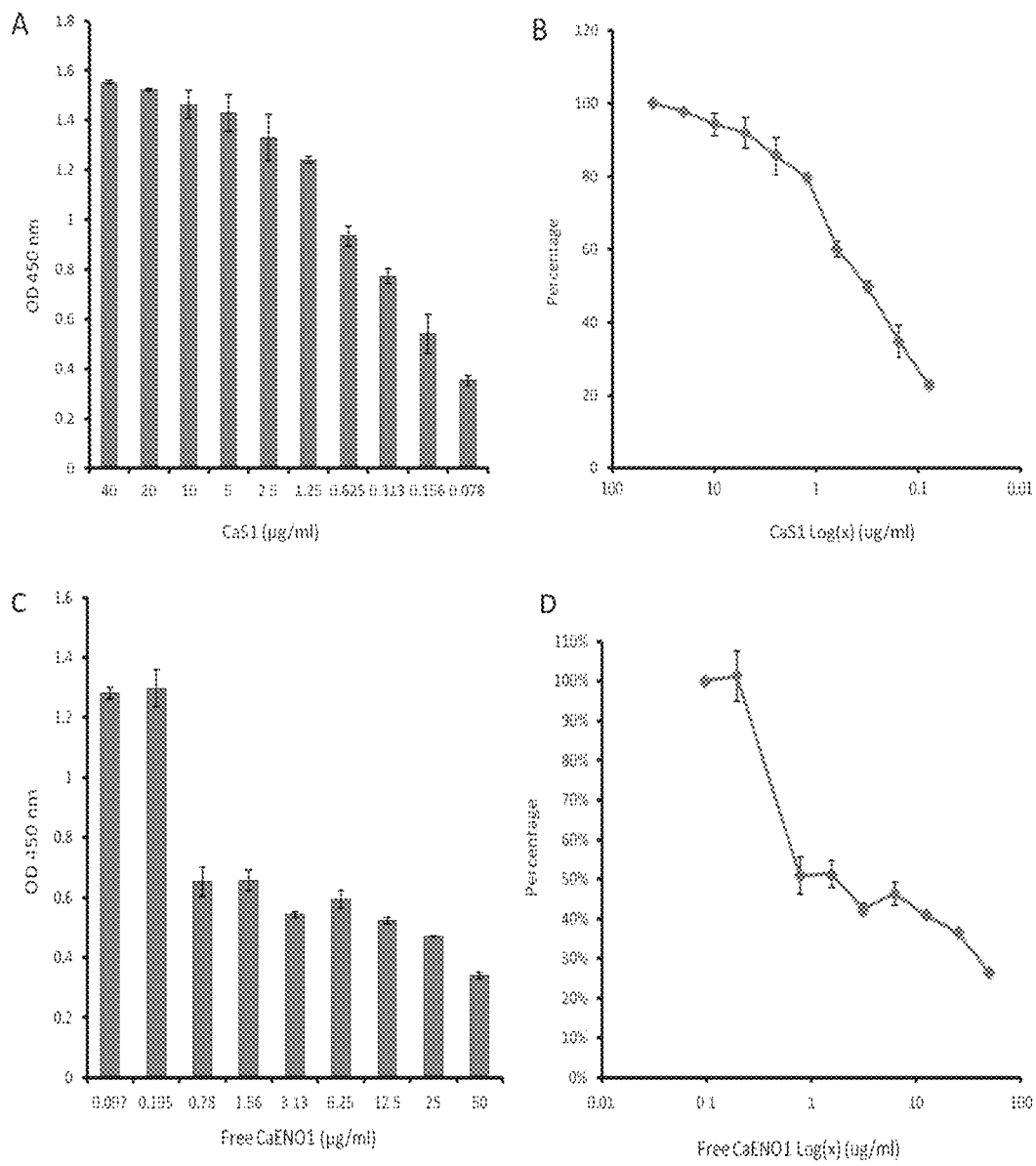
FIG. 5 (A) to (D) shows $K_D$ determination of CaS1 scFv by ELISA and competitive ELISA. (A) Purified CaS1 scFv was used to recognize recombinant CaENO1 protein. The CaS1 scFv were used as primary antibody with series dilution. The goat anti-chicken light chain IgG was used as secondary antibody. The HRP conjugated donkey anti-goat IgG was used to decet. (B) OD value was calculated into percentage. $K_D$ of CaS1 scFv is 0.498 ug/ml=$1.88 \times 10^{-8}$ M. (C) CaS1 scFv was used to recognize series diluted free form recombinant CaENO1 protein that competed with fixed form recombinant CaENO1 protein. The goat anti-chicken light chain IgG was used as secondary antibody. The HRP conjugated donkey anti-goat IgG was used to detect. (D) We calculated OD value into percentage. $K_D$ of CaS1 scFv is 4.45 ug/ml=$8.9 \times 10^{-8}$ M. ELISA data were represented as mean±SD of the duplicated well.

The antibody purified from the chicken includes framework region (FR) and complementarity determining regions (CDRs). Colonies #1S1 to #1S12 were isolated and sequenced using ompseq primers (5'-AAGACAGC-TATCGCGATTGCAGTG-3'), and the sequencing results were analyzed by BioEdit software and then the resulting sequences were compared with chicken germline. It was milk was added to the wells, and the plate was incubated at 37° C. for 1 hour for blocking. Meanwhile, 1 µg/mL CaS1 was incubated with each 2-fold and 10 times serial diluted samples from 50 µg/mL free form His-CaENO1 (i.e., 50 µg/mL, 25 µg/mL, 12.5 µg/mL, 6.25 µg/mL, 3.13 µg/mL, 1.56 µg/mL, 0.78 µg/mL, 0.39 µg/mL, 0.19 µg/mL of free form His-CaENO1) at room temperature for 1 hour. Then, these samples were added to the coated and blocked wells described above and incubated at 37° C. for 1 hour for conducting a competition reaction. Thereafter, the wells were washed with PBST 6 times; then, goat anti-chicken light chain (1:3000 diluted) was added thereto and incubated at 37° C. for 1 hour. Thereafter, the wells were washed with PBST 6 times; then donkey anti-goat HRP antibody (1:5000 diluted) was added thereto and incubated at 37° C. for 1 hour. Thereafter, the wells were washed with PBST 6 times; then, the color reaction was initiated by adding 3,3',5,5'-Tetramethylbenzidine (TMB), and the reaction was terminated by iN HCl. The absorbance at 450 nm wavelength was detected to get $OD_{450}$. To determine the binding activity of CaS1 to CaENO1, ELISA (FIGS. 5A-B) and competitive ELISA (FIG. 5C-D) were performed. As seen in FIGS. 5A and 5B, the binding activity of CaS1 scFv antibody to CaENO1 were concentration dependent, and the $K_D$ are $1.88 \times 10^{-8}$ M and $8.9 \times 10^{-8}$ M, respectively as measured by ELISA and competitive ELISA.

Example 6 CaS1 scFv Binding to Cell Lysate of C. albicans and C. tropicalis

Figure 6:
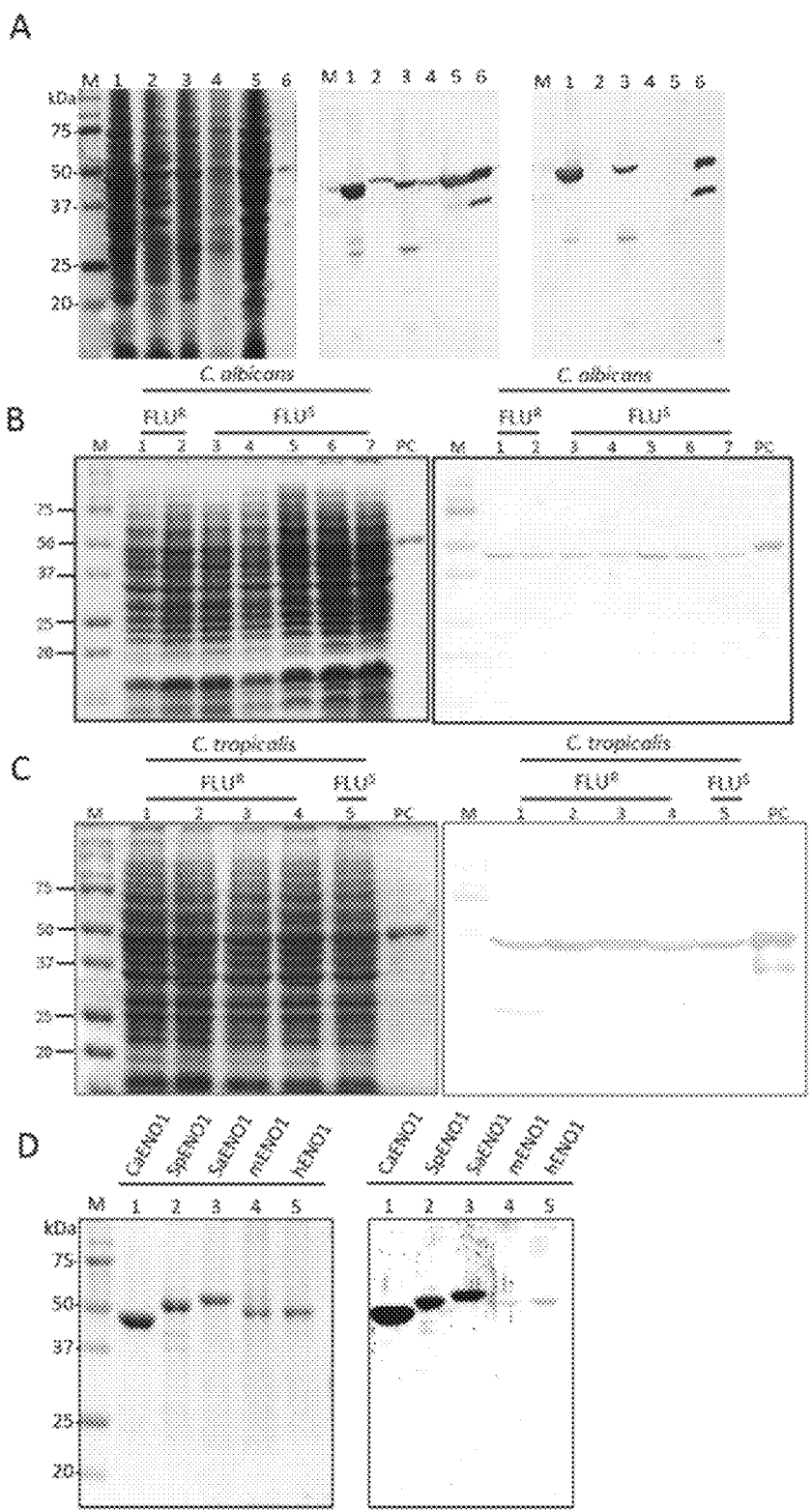
FIG. 6 (A) to (D) shows binding activity of CaS1 scFv against ENO1 proteins on *Candida* spp. by Western blot. (A) The total cell lysates of 5 *Candida* spp. were visualized on SDS-PAGE (left). After transferred onto the NC membranes, they were probed with purified anti-CaENO1 from 7th immunized chicken (1:3,000) (middle), or with CaS1 scFv (right) as described in material and methods. Lanes 1-6 in (A) contained the total cell lysates of *C. albicans, C. krusei, C. tropicalis, C. parapsilosis* and *C. glabrate* and purified recombinant CaENO1, respectively. (B) Total cell lysate from fluconazole resistant ($FLU^R$) and fluconazole susceptible ($FLU^S$) *C. albicans* (lanes 1-7 represent CA6-17, CA7-26, CA7-3, CA10-50, CA7-30, CA10-65, SC5314, respectively) by SDS-PAGE (left) and probed with CaS1 scFv by Western blot (right). (C) Total cell lysate from $FLU^R$ and $FLU^s$ and *C. tropicalis* (lanes 1-5 represent CT6-29, CT11-52, CT6-50, CT12-54, BCRC20520, respectively) by SDS-PAGE (left) and probed with CaS1 scFv by Western blot (right). (D) The purified ENO1 proteins of *C. albicans, S. pneumonia, S. aureus*, mouse and human were visualized on SDS-PAGE (left). After transferred onto the NC membranes, they were probed with purified CaS1 scFv (right) as described. Lane M contained protein markers.

This CaS1 scFv was evaluated for its binding activity to different species of Candida. Five common strains of Candida were obtained, total lysate of five species Candida were analyzed on SDS-PAGE (FIG. 6A left) and subsequent Western blot. As seen in FIG. 4A middle, anti-CaENO1 polyclonal IgY are able to recognize five species of Candida tested as expected. However, CaS1 scFv can only reacted with C. albicans as seen in FIG. 6A right lane 1 and C. tropicalis as seen in lane 3. This CaS1 scFv cannot react with C. krusei (lane 2), C. parapsilosis (lane 4) and C. glabrate (lane 5). The ENO1 protein sequence between C. albicans and C. tropicalis are 83% homology, therefore, the reason that CaS1 can recognized C. albicans as well as C. tropicalis may suggest these two species share similar epitope which can bind to CaS1 scFv.

Furthermore, we exame the CaS1 scFv binding activity to fluconazole resistance and susceptible stains of Candida spp. from clinic. The Candida spp. and their MIC were listed in Table 2. As shown in FIG. 4D-G, CaS1 scFv can bind to fluconazole resistance and susceptible C. albicans (FIG. 6B) and C. tropicalis (FIG. 6C) but not to C. glabrate and C. parapsilosis (data not shown). These data suggesting CaS1 scFv can be potentially used for the diagnosis and/or treatment of the fluconazole resistance C. albicans and C. tropicalis.

In addition, we also observed that CaS1 scFv can bind to different species of ENO1 as seen in FIG. 6D. ENO1 for C. albicans (CaENO1), S. pneumoniae (SpENO1), S. aureus (SaENO1), mouse (mENO1) and human (hENO1) were purified and subjected on SDS-PAGE (FIG. 6D left) and Western blot (FIG. 6D right). CaS1 scFv bind not only CaENO1 but also SpENO1 and SaENO1, but very little to mENO1 and hENO1 (FIG. 6D right). These results suggest that ENO1 from C. albicans, S. pneumoniae and S. aureus, may share similar epitope which can bind to CaS1 scFv.

TABLE 2

Clinical fluconazole resistance and susceptible Candida spp. and their MIC.

| Specimen | organism | drug | MIC (μg/ml) | Interpretation* |
|---|---|---|---|---|
| CA6-17 | C. albicans | fluconazole | 16 | R |
| CA7-26 | C. albicans | fluconazole | 8 | R |
| CA7-3 | C. albicans | fluconazole | 2 | S |

TABLE 2-continued

Clinical fluconazole resistance and susceptible Candida spp. and their MIC.

| Specimen | organism | drug | MIC (μg/ml) | Interpretation* |
|---|---|---|---|---|
| CA10-50 | C. albicans | fluconazole | 2 | S |
| CA7-30 | C. albicans | fluconazole | 1 | S |
| CA10-65 | C. albicans | fluconazole | 1 | S |
| CT6-29 | C. tropicalis | fluconazole | 32 | R |
| CT11-52 | C. tropicalis | fluconazole | 32 | R |
| CT6-50 | C. tropicalis | fluconazole | 8 | R |
| CT12-54 | C. tropicalis | fluconazole | 8 | S |
| CG5-8 | C. glabrate | fluconazole | 64 | R |
| CG8-11 | C. glabrate | fluconazole | 64 | R |
| CG7-37 | C. glabrate | fluconazole | 32 | S |
| CG5-66 | C. glabrate | fluconazole | 16 | S |
| CP8-20 | C. parapsilosis | fluconazole | 256 | R |
| CP12-37 | C. parapsilosis | fluconazole | 256 | R |
| CP6-20 | C. parapsilosis | fluconazole | 16 | R |
| CP7-17 | C. parapsilosis | fluconazole | 8 | S |
| CP8-48 | C. parapsilosis | fluconazole | 4 | S |

*R for resistance; S for susceptible.

Example 7 Flow Cytometry Assay for Identification of CaS1 Antibody to Alpha-Enolase on Cell Surface of C. Albicans Anti-CaENO1 IgY, scFv CaS1 and control scFv were contacted with C. albicans and then subjected to flow cytometry assay. Anti-CaENO1 IgY, scFv CaS1 and control scFv show 89.7+/−2.8%, 46.64+/−3.1% and 23+/−2.3% FITC fluorescence reaction (FIG. 7A), representing that the antibody can bind to alpha-enolase on the surface of C. albicans. Moreover, propidium iodide for dying was used to identify the mortality rate of C. albicans, and it was found that Anti-CaENO1 IgY, scFv CaS1 and control scFv kill 90+/−1.5%, 37+/−0.8%, 21+/−1% of C. albicans (FIG. 7A). As shown in FIG. 7B, in comparison with control svFv and Anti-CaENO1 IgY, scFv CaS1 can bind to the alpha-enolase on the surface of C. albicans and thus kill them.

Figure 8:
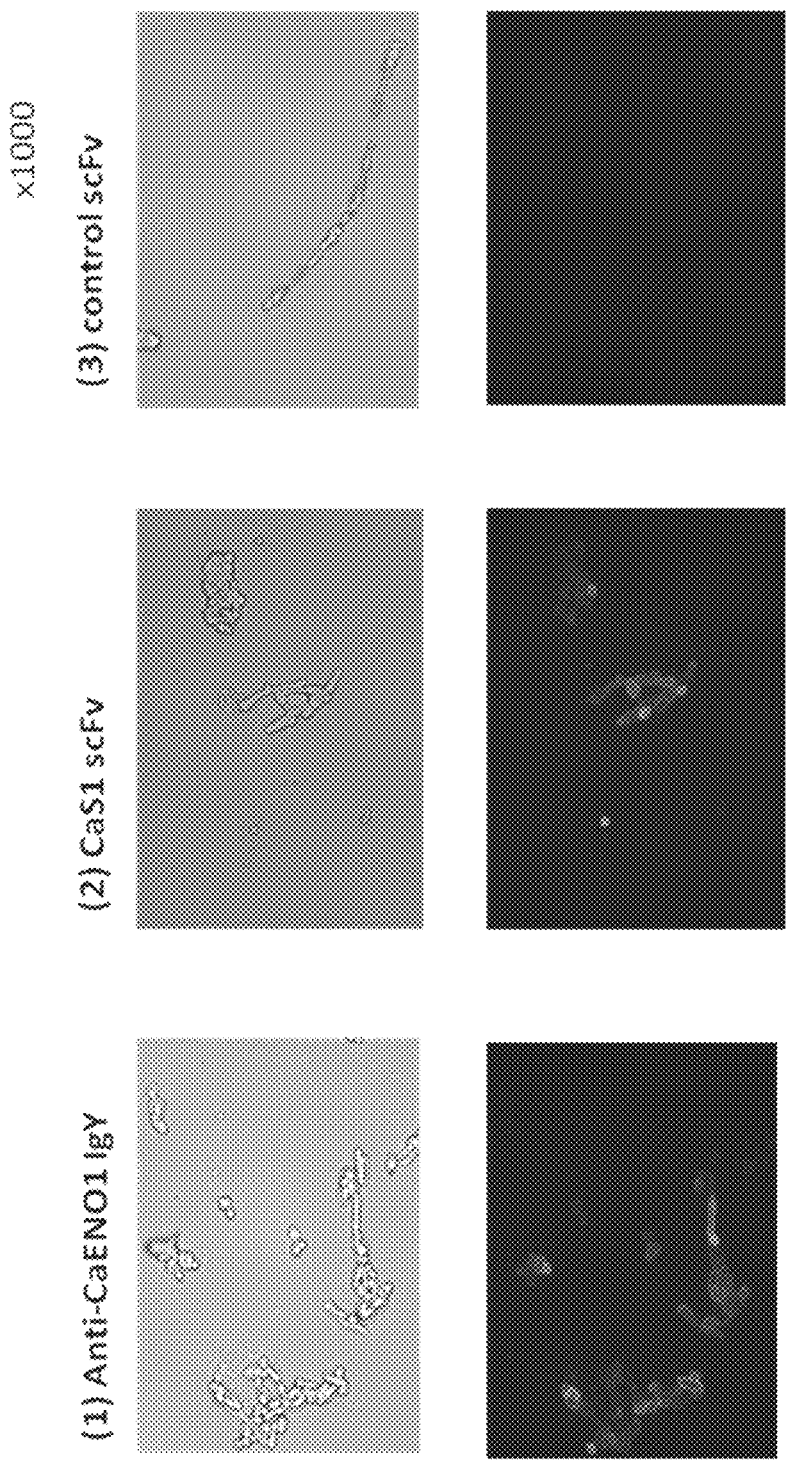
FIG. 8 shows analysis of scFv CaS1 to *C. albicans* by immunofluorescence staining. Anti-CaENO1 antibodies were used to detect alpha-enolase protein on *C. albicans* cell surface ENO1. (1) Detected with anti-CaENO1 IgY and developed by FITC conjugation rabbit anti-chicken antibodies. (2) Detected with scFv CaS1 and developed by goat anti-chicken light chain antibodies and FITC rabbit anti-goat antibodies. (3) An irrelevant scFv was used on negative control.

Example 8 Immunofluorescence Assay for Identification of CaS1 Antibody to Alpha-Enolase on Cell Surface of C. Albicans Anti-CaENO1 IgY, scFv CaS1 and control scFv were used in immunofluorescence assay for identification of CaS1 antibody to alpha-enolase on cell surface of C. albicans. As shown in FIG. 8, anti-CaENO1 IgY (1) and scFv CaS1 (2) bind to the alpha-enolase on the surface of C. albicans, whereas the control scFv (3) does not show the binding.

Example 9 Attenuation of C. albicans Growth and Hyphal Formation by CaS1 scFv We evaluated the influence of CaS1 on growth of C. albicans, we pre-incubated CaS1 scFv with C. albicans and plated on the agar. As seen in FIG. 9A, CaS1 scFv decreased C. albicans growth as observed on YPD agar plate when diluted to the 10-4 as compared to control. The inhibitory effects for anti-CaENO1 IgY is as good as scFv CaS1 scFv.

Hyphal formation has also been shown to play a critical role in the virulence of the C. albicans. So we further investigated whether CaS1 scFv affects the hyphal formation. We pre-incubated CaS1 scFv with C. albicans and the colony morphology was examined. As seen in Figure. 9B, along the edge of the control colony, hyphae were clearly visible, whereas very little or none were observed for the CaS1 scFv treated colonies. The attenuation effect for hyphae formation is obvious when CaS1 scFv were pre-incubated with C. albicans.

Figure 10:
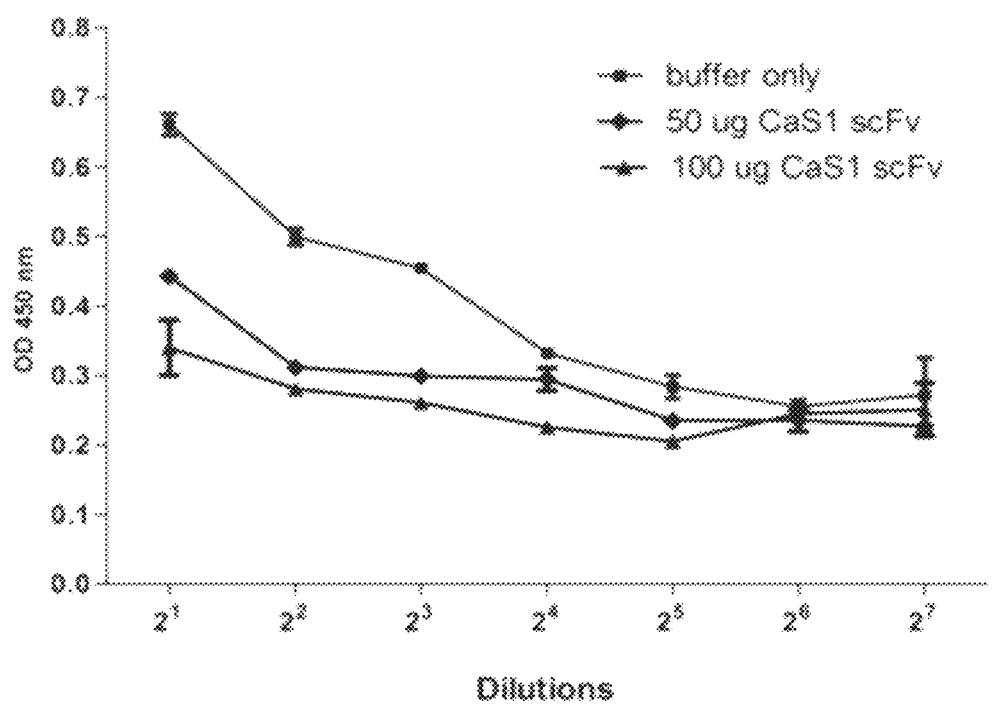
FIG. 10 shows CaS1 ScFv inhibited *C. albicans* adhesion to oral epidermal cells. *C. albicans* were mixed with 1×PBS, 50 ug or 100 ug CaS1 scFv at 37° C. for 1 hr and added into OECM-1 cells in culture wells as described in the text. After being washed, cells attached to *C. albicans* were detected by adding HRP-conjugated anti-*C. albicans* antibodies.

Example 10 Inhibition of Binding of C. Albicans to Human Oral Keratinocyte OECM-1 Cells C. albicans cells ($1\times10^6$) were treated with 50 μg and 100 μg of scFv CaS1, respectively, and the resulting mixtures were added to human oral keratinocyte OECM-1 cells to test the binding ability of C. albicans cells to OECM-1 cells. In comparison with the PBS control, the 50 μg and 100 μg of scFv CaS1 significantly reduced the binding of C. albicans cells to OECM-1 cells (FIG. 10).

Example 11 Effect of CaS1 scFv on the Binding of ENO1 to Plasminogen

It is well known that surface ENO1 act as a plasminogen receptor 32, binding to plasminogen will activate it to plasmin and leading to the degradation of the fibrinogen (extracellular matrix) containing in the gel. We performed matrix-gel studies to test the possible biological significance of CaENO1-plasminogen association and the effect of CaS1 scFv on this binding was observed.

Figure 11:
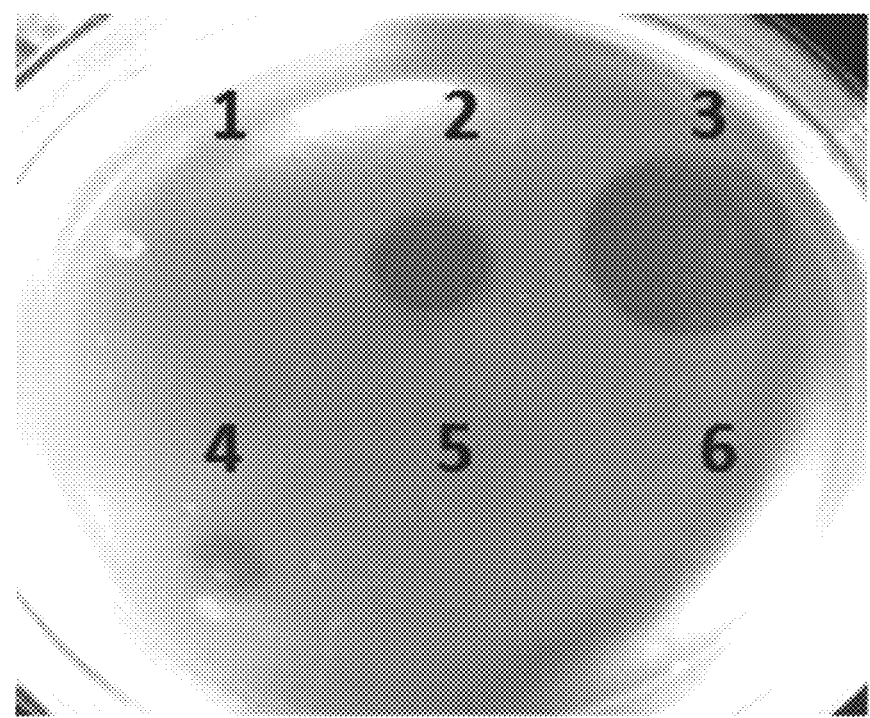
FIG. 11 shows the effect of CaS1 scFv on the binding of ENO1 to plasminogen. The ability of CaS1 scFv to block the binding of CaENO1 with plasminogen was evaluated by fibrin matrix-gel degradation analysis. Various samples containing *C. albicans* only (1), *C. albicans*+1 ug of plasminogen (2) or *C. albicans*+10 ug of plasminogen (3) were spotted on the plate. Similar experiments were carried out except *C. albicans* were mixed first with 10 ug (4) or 100 ug (5) of CaS1 scFv, followed by the addition of 10 ug of plasminogen. *C. albicans*+CaS1 scFv without plasminogen (6) were spotted as a negative control.

A representative plate was seen in FIG. 11. In the absence of plasminogen, Candida alone (FIG. 11-1) or CaS1 scFv alone (FIG. 9-6) showed no fibrinolysis activity. C. albicans incubated with 1 and 10 μg of plasminogen, resulted in a significant increase in fibrinolytic activity (FIGS. 11-2 and 11-3). This result suggests that CaENO1 bound plasminogen can be activated by thrombin, present in the matrix gel, to digest the surrounding fibrinogen. However, fibrinolytic activities can be significantly inhibited by pre-incubated C. albicans with CaS1 (10 and 100 g) as compared to in the presence of plasminogen alone as show in FIGS. 11-4 and 11-5. The inhibition of the degradation of the fibrinogen in the gel is obvious. Our results suggest that binding of CaENO1 to plasminogen was significantly reduced by CaS1 scFv antibodies in a dose-dependent manner.

Example 12 Neutralization of C. Albicans Toxicity by ScFv CaS1 to Extend Survival Rate of Infected Mice $1\times10^6$ cells of C. albicans solutions were mixed with 100 μg of each of the anti-CaENO1 IgY, scFv CaS1 and control scFv and then injected into ICR mice (5 mice for each group). After 10 days, the survival rates of the anti-CaENO1 IgY, scFv CaS1 and control scFv groups were 100%, 80% and 0%, respectively. It was found that the anti-CaENO1 IgY and scFv CaS1 can neutralize the toxicity of C. albicans and thus can extend the life of mice or protect the mice from death.

Example 13 Humanization of CaS1 scFv by CDR Grafting

Two humanized CaS1 scFv (V1 and V3) were designed. Humanized CaS1 scFv V1 was grafted onto human framework (Protein Data Bank: 2JIX-L, 2ZKH-H), this most suitable length sequence was analyzed by Discovery Studio software. Humanized CaS1 scFv V3 was grafted onto human framework that the sequence of Avastin® (Protein Data Bank: 2FJG). These humanized CaS1 scFv (V1 and V3) were synthesized by Gemonics BioSci & Tech (New Taipei City, Taiwan), cloned into pComb3X vector, and transferred into Top 10 E. coli for protein expression. The expressed V1 and V3 proteins were purified by $Ni^+$ sepharose and analyzed by SDS-PAGE and Western blot.

Figure 12:
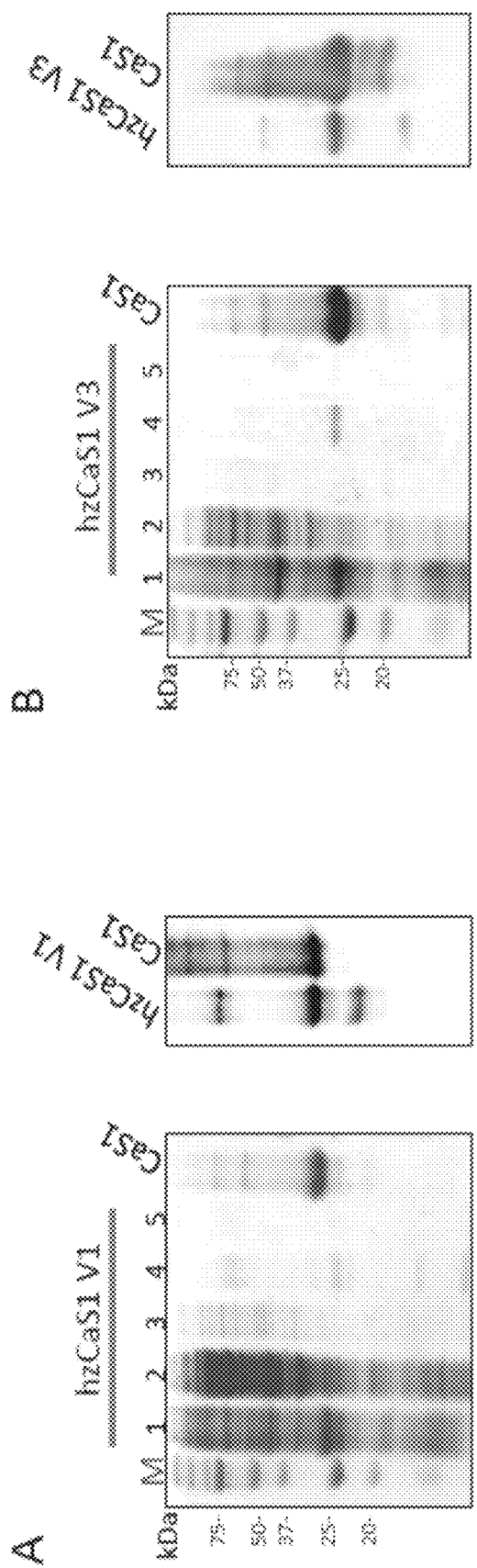
FIGS. 12 (A) and (B) shows the expression and purification of hzCaS1 V1 and V3 scFv. After expression and sonication, $Ni^+$ sepharose was used to purify hzCaS1 V1 (A) and V3 (B) scFv. The Coomassie blue was used to stain (left panel). The mouse anti-HA IgG and HRP conjugated rabbit anti-mouse IgG in the Western blot (right panel). The arrow denoted hzCaS1 scFv molecular weight about 25 kDa. Lane 1: hzCaS1 scFv clone cell lysate. Lane 2: supernatant of hzCaS1 scFv after $Ni^{2+}$ sepharose binding. Lane 3: collection of first time washing buffer. Lane 4: collection of first elution buffer. Lane 5: $Ni^+$ sepharose after elution. Positive control: CaS1 scFv.

As the results shown in FIG. 12, the humanized CaS1 scFv V1 (FIG. 13A) and V3 (FIG. 13B) antibodies were designed to synthesize a plasmid DNA with the target gene, and the DNA was then transferred into Top 10 E. coli for expression. Then, the expressed protein was purified with $Ni^+$ Sepharose, and analyzed by SDS-PAGE. Afterward, the expressed protein was confirmed by Western blot (anti-HA tag).

Example 14 Determination Binding Ability of CaENO1 with hzCaS1 V1 and V3

Figure 13:
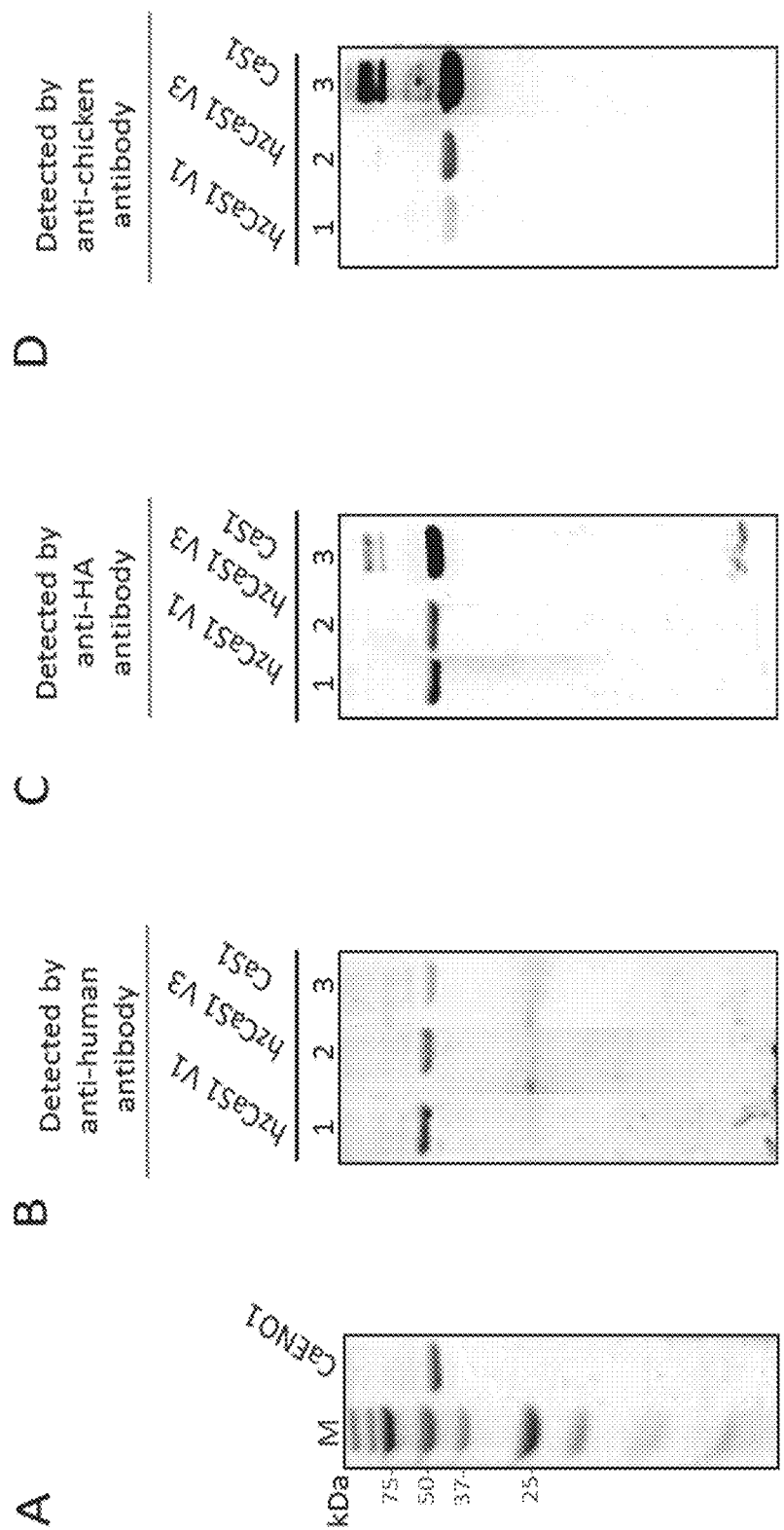
FIG. 13 shows determination binding affinity CaENO1 with hzCaS1 V1, V3. The hzCaS1 V1, V3 and CaS1 scFv were used to recognize recombinant CaENO1 protein. (A) The Coomassie blue was used to stain. (B) The mouse anti-human κ, λ IgG and the HRP conjugated rabbit anti-mouse IgG was used in the Western blot (right panel). (C) The mouse anti-HA IgG and HRP conjugated rabbit anti-mouse IgG was used. (D) The goat anti-chicken light chain IgG and HRP conjugated donkey anti-goat IgG was used. Lane 1: hzCaS1 scFv V1. Lane 2: hzCaS1 scFv V3. Lane 3: CaS1 scFv.

The hzCaS1 V1, V3 and CaS1 scFv were used to recognize recombinant CaENO1 protein. As shown in FIG. 13, (A) the Coomassie blue was used to stain; (B) the mouse anti-human κ, λ IgG and the HRP conjugated rabbit anti-mouse IgG was used in the Western blot (right panel); (C) the mouse anti-HA IgG and HRP conjugated rabbit anti-mouse IgG was used; and (D) The goat anti-chicken light chain IgG and HRP conjugated donkey anti-goat igG was used. Lane 1: hzCaS1 scFv V1. Lane 2: hzCaS1 scFv V3. Lane 3: CaS1 scFv.

Example 15 $K_D$ Determination of hzCaS1 V1 and V3 scFv by ELISA

Figure 14:
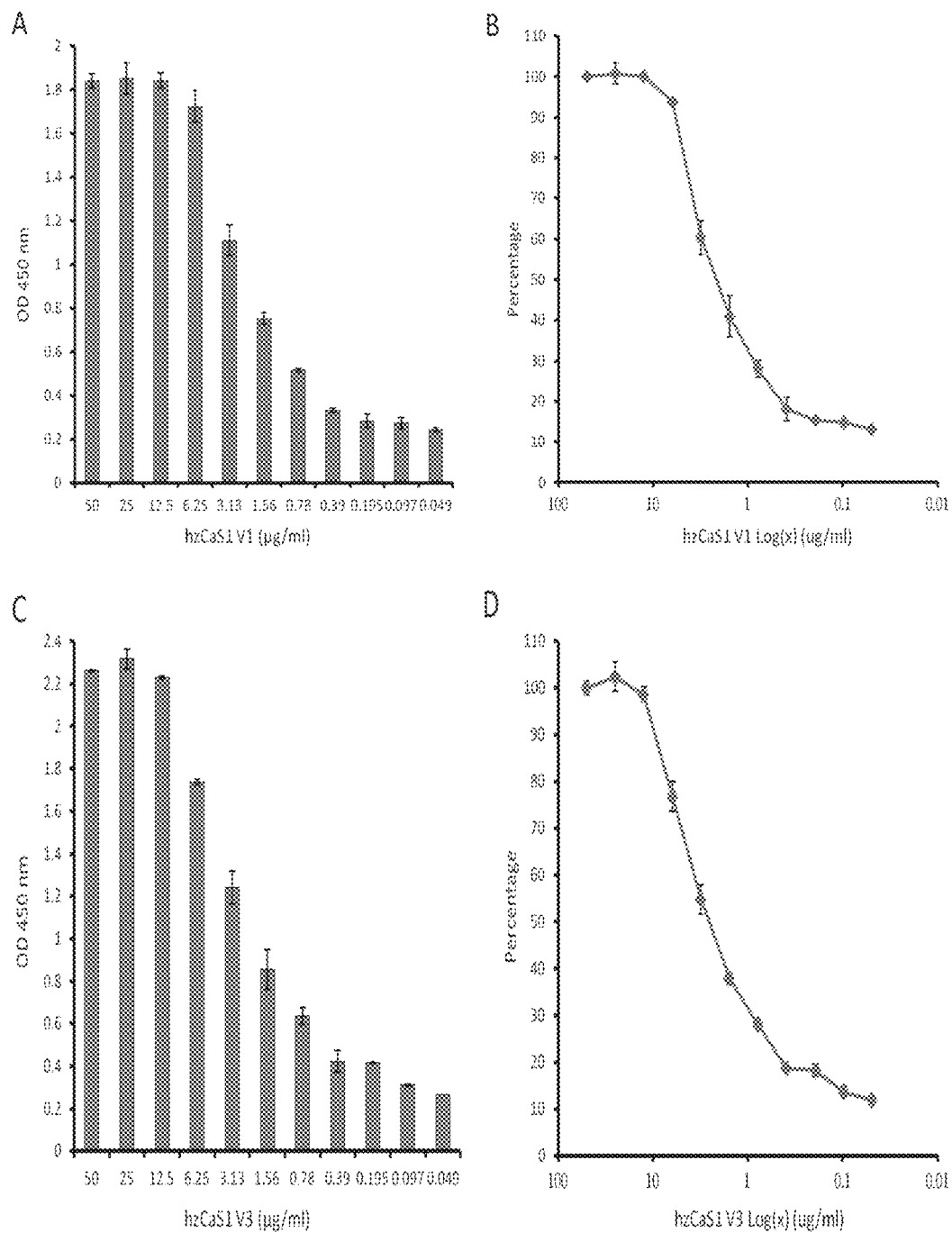

Purified hzCaS1 V1 and V3 scFv were used to recognize recombinant CaENO1 protein. The hzCaS1 V1 and V3 scFv were used as primary antibody with series dilution. The goat anti-chicken light chain IgG was used as secondary antibody. The HRP conjugated donkey anti-goat IgG was used to decet (see FIGS. 14 (A) and (C)). OD value was calculated into percentage. The $K_D$ or 50% effective concentration ($EC_{50}$) of scFv were calculated and expressed by molarity (M). $K_D$ of hzCaS1 V1 and V3 scFv is 1.51 ug/ml=$4.6\times10^{-8}$ M and 2.12 ug/ml=$8.4\times10^{-8}$ M, respectively. ELISA data were represented as mean±SD of the duplicated well (see FIGS. 14 (B) and (D)).

Figure 1:
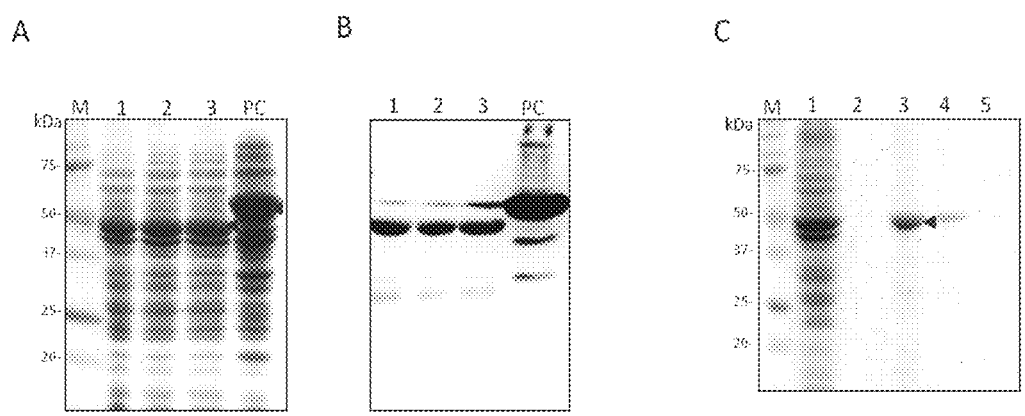
FIG. 1 (A) to (C) shows the expression and purification of recombinant CaENO1 protein. (A) Expression of recombinant CaENO1 protein was induced by 0.1 (Lane 1), 0.5 (Lane 2), and 1.0 mM IPTG (Lane 3). The Coomassie blue was used to stain. (B) The mouse anti-His IgG and HRP conjugated rabbit anti-mouse IgG were used in Western blot. Positive control: recombinant SaENO1 protein. (C) After expression and sonication, we used Ni$^+$ sepharose to purify recombinant CaENO1 protein. Lane 1: supernatant of CaENO1 clone after Ni$^{2+}$ sepharose binding. Lane 2: collection of first time washing buffer. Lane 3: collection of first elution buffer. Lane 4: second time elution buffer. Lane 5: denoted Ni$^+$ sepharose after elution. The arrow denoted the recombinant CaENO1 protein molecular weight about 50 kDa.

Example 16 CaS1, hzCaS1 V1 and V3 scFv Inhibits CaENO1 Binding to Plasminogen CaENO1 on $Ni^+$ sepharose was treated with 100 ug hzCaS1 V1, V3 and CaS1 scFv for 1 hour, following incubating with plasminogen (20 ug) for 1 hour. Each experimental group of CaENO1 with CaS1 scFv were dropped onto gel and incubated at room temperature for 2 days to observe gel degrade result an the results are shown in FIG. 15. FIG. 15-1 in the presence of plasminogen (1 ug/ul) alone (positive control) show a significant fibrinolytic activity as seen in the gel. FIG. 15-2 CaENO1 on Ni Sepharose™ (10 ug) alone (negative control) with no plasminogen show no fibrinolysis activity in the gel. FIG. 15-3 CaENO1 on Sepharose™ (10 ug) with plasminogen (20 ug) show fibrinolytic activity. FIG. 15-4,5,6 CaENO1 on Sepharose™ (10 ug) treated with hzCaS1 V1 (FIG. 15-4), V3 (FIG. 15-5), CaS1 scFv (FIG. 15-6) (100 ug) and incubated with plasminogen (20 ug) show no fibrinolytic activity as compared to 15-3. Therefore, result suggests that CaENO1 bound plasminogen can be activated by thrombin, present in the matrix gel, to digest the surrounding fibrinogen. However, fibrinolytic activities can be significantly inhibited by pre-incubated CaENO1 with hzCaS1 V1, V3, CaS1 scFv as compared to in the presence of plasminogen as show in FIG. 15-3. The inhibition of the degradation of the fibrinogen in the gel is obvious (FIG. 15-4,5,6). Our results suggest that binding of CaENO1 to plasminogen was significantly reduced by hzCaS1 V1, V3, CaS1 scFv antibodies.

Example 17 Epitope Mapping of CaENO1 Using CaS1 scFv

Nine PCR-amplified fragments were obtained using full-length CaENO1 (1323 bp) as template, ligated into PET-21a vector and transformed into BL-21 *E. coli*. The identity of inserted fragments was confirmed by sequencing (Genomics BioSci & Tech, New Taipei City, Taiwan). Protein expression was carried out by IPTG induction. SDS-PAGE and Western blot were used to characterize the expressed recombinant proteins.

For epitope mapping of CaENO1, the purified CaS1 scFv was used to recognize recombinant CaENO1 protein on Western blot and ELISA. The epitope region was mapped to contain 198 bp nucleotides, which deduced amino acid sequences (residues 235 to 300) are DKAGYKGKVGI-AMDVASSEFYKDGKYDLDFKNPESDPSKWLSGPQL-ADLYEQLISEYPIVS IEDPF (SEQ ID NO:19) (66 amino acids).

To further determine the epitopic location, site directed mutagenesis (Kunkel method) was used to construct nine peptide-expressing phages according to the nucleotide sequences of 198 bp of mapped antigenic fragment above mentioned with minor modification ("Chapter 2, Constructing phage display libraries by oligonucleotide-directed mutagenesis" on Phage Display-A Practical Approach, edited by Tim Clackson and Henry B. Lowman, OXFORD University Press 2004). The modified pCANTAB 5E DNAs carrying nucleotide sequences coding the antigenic epitopes were transformed into ER2738 *E. coli*. The phagemid DNAs were extracted from *E. coli* and analyzed for insertion with EcoRI enzyme restriction. Each resulting phage expressing 10 amino acids on viral particle surface was examined for their reactivity against CaS1 scFv antibody on ELISA. The combined results showed CaS1 scFv recognized the amino acid residues on antigenic epitopes located among $_{240}$KG-KVGIAMDV$_{249}$ (SEQ ID NO:3) and $_{278}$PQLADLYEQLI-SEYP$_{292}$ (SEQ ID NO:4).

Nine recombinant CaENO1 proteins as above were used to recognize the purified plasminogen on dot blot. The results showed CaS1 scFv antibody binds to a fragment of plasminogen spanning amino acid residues 301 to 437, which sequences are AEDDWDAWVHFFERVGDKIQI-VGDDLTVTNPTRIKTAIEKKAANALLLKVNQIGTLTE-SIQ AANDSYAAGWGVMVSHRSGETEDTFIADLSV-GLRSGQIKTGAPARSERLAKLNQILRIEEEL GSEAI-YAGKDFQKA (SEQ ID NO:20). The above results are shown in FIG. 16.

Example 18 CaS1 scFv Prolongs the Survival Rate of ICR Mice Infected with *C. albicans*

We evaluated the survival rate of the CaS1 on animal model. Initially ICR mice were tail-vein injected with $1\times10^6$ cells of *C. albicans* with PBS alone or cells pre-incubated with CaS1 (10 and 100 µg) for one hour at 37° C. As seen in FIG. 17, pre-incubated with CaS1 (10 and 100 µg) pro-long the survival rate of mice to 40% and 80% respectively, as compared to PBS control. Anti-Deinagkistrodon acutus scFv (anti-DA) is an antibody to snake venom, which was used as an unrelated scFv control. These data suggest CaS1 scFv provide partial protect activity against lethal challenge of candidemia on ICR mice.

Example 19 *Candida albicans* Biofilm Formation Inhibition Assay

*Candida albicans* cells were cultured in YPD medium and then collected. The cells were washed with PBS and resuspended in YPD medium containing 100 mM glucose at a cell density of $10^7$ cells/ml. A 96-well plate was treated with CaS1 scFv or fluconazole and then inoculated with 1 ml of the cell suspension. After a two-hour adhesion period, the inoculum was removed by washing with PBS, and YPD medium containing 100 mM glucose was applied to the plate. The plate was treated with CaS1 scFv or fluconazole and biofilms were grown for 72 hours at 37° C. The plate was washed with PBS, and then biofilm formation was observed by microscopy (FIG. 18).

What is claimed is:

1. A polypeptide consisting of an epitope, consisting of $_{283}$LYEQLISEYP$_{292}$ (SEQ ID NO:1), $_{278}$PQLADLYEQL$_{287}$ (SEQ ID NO:2), $_{240}$KGKVGIAMDV$_{249}$ (SEQ ID NO:3) or $_{278}$PQLADLYEQLISEYP$_{292}$ (SEQ ID NO:4).

2. A pharmaceutical composition comprising the polypeptide of claim 1 and a pharmaceutically acceptable carrier, excipient or adjuvant.

3. The pharmaceutical composition of claim 2, which is a vaccine.

4. The pharmaceutical composition of claim 2, which further comprises one or more additional anti-*Candida*, anti-*Streptococcus* or anti-*Staphylococcus* drugs.

5. The pharmaceutical composition of claim 4, wherein the additional anti-*Candida* drug is fluconazole, itraconazole, posaconazole, echinocandins, voriconazole, lipid formulations of amphotericin B, Ketoconazole, clotrimazole, econazole, ciclopirox, or nystatin.

6. The pharmaceutical composition of claim 5, wherein the echinocandin is caspofungin, micafungin, anidulafungin or ciclopirox.

* * * * *